(12) United States Patent
Aihara et al.

(10) Patent No.: US 8,735,577 B2
(45) Date of Patent: May 27, 2014

(54) 1,3,5-TRIAZINE DERIVATIVE, PROCESS FOR PRODUCING SAME, AND ORGANIC ELECTROLUMINESCENT ELEMENT COMPRISING SAME AS CONSTITUENT COMPONENT

(75) Inventors: Hidenori Aihara, Ayase (JP); Akitoshi Ogata, Ayase (JP); Tsuyoshi Tanaka, Ayase (JP)

(73) Assignees: Tosoh Corporation, Yamagushi (JP); Sagami Chemical Research Institute, Kanagawa (JP)

( * ) Notice: Subject to any disclaimer, the term of this patent is extended or adjusted under 35 U.S.C. 154(b) by 329 days.

(21) Appl. No.: 13/122,246

(22) PCT Filed: Oct. 2, 2009

(86) PCT No.: PCT/JP2009/067219
§ 371 (c)(1),
(2), (4) Date: Apr. 1, 2011

(87) PCT Pub. No.: WO2010/038854
PCT Pub. Date: Apr. 8, 2010

(65) Prior Publication Data
US 2011/0190494 A1    Aug. 4, 2011

(30) Foreign Application Priority Data

Oct. 3, 2008 (JP) ................................. 2008-258652
Oct. 3, 2008 (JP) ................................. 2008-258653

(51) Int. Cl.
| | | |
|---|---|---|
| C07D 251/24 | (2006.01) | |
| C07D 403/04 | (2006.01) | |
| C07D 403/14 | (2006.01) | |
| C07D 401/14 | (2006.01) | |
| C09K 11/06 | (2006.01) | |
| C07B 61/00 | (2006.01) | |
| H01L 51/50 | (2006.01) | |

(52) U.S. Cl.
USPC .................. 544/180; 345/82; 345/76; 345/72

(58) Field of Classification Search
USPC .................. 544/180; 345/82, 76; 514/82, 76
See application file for complete search history.

(56) References Cited

U.S. PATENT DOCUMENTS

| | | | |
|---|---|---|---|
| 6,057,048 A | 5/2000 | Hu | |
| 6,225,467 B1 | 5/2001 | Esteghamatian et al. | |
| 6,229,012 B1 | 5/2001 | Hu | |
| 7,994,316 B2 * | 8/2011 | Yamakawa et al. | 544/180 |
| 8,268,997 B2 * | 9/2012 | Yamakawa et al. | 544/180 |
| 2009/0281311 A1 | 11/2009 | Yamakawa et al. | |
| 2010/0249406 A1 | 9/2010 | Yamakawa et al. | |

FOREIGN PATENT DOCUMENTS

| | | |
|---|---|---|
| JP | 6-136359 | 5/1994 |
| JP | 6-207169 | 7/1994 |
| JP | 7-157473 | 6/1995 |
| JP | 2001-143869 | 5/2001 |
| JP | 2003-45662 | 2/2003 |
| JP | 2003-282270 | 10/2003 |
| JP | 2003-303689 | 10/2003 |
| JP | 2004-022334 | 1/2004 |
| JP | 2004-63465 | 2/2004 |
| JP | 2005-104986 | 4/2005 |
| JP | 2006-199677 | 8/2006 |
| JP | 2007-137829 | 6/2007 |
| JP | 2007-223929 | 9/2007 |
| JP | 2007-314503 | 12/2007 |
| JP | 2009-224512 | 10/2009 |
| WO | 95/25097 | 9/1995 |
| WO | 2004/080975 | 9/2004 |
| WO | 2007/023840 | 3/2007 |
| WO | 2008/129912 | 10/2008 |

OTHER PUBLICATIONS

JP 2007-137829 published Jul. 6, 2007—Machine Translation.*
Search report from E.P.O. that issued with respect to patent family member European Patent Application No. 09817886.6, mail date is Mar. 8, 2012.
U.S. Appl. No. 13/131,972 to Hidenori Aihara et al., filed May 31, 2011.
Kenji Okumoto et al., "Green Fluorescent Organic Light-emitting Device with External Quantum Efficiency of Nearly 10%", American Institute of Physics (Applied Physics Letters 89), 2006, pp. 063504-1-063504-3.
Bibliographic data: JP 4106974 (Abstract of JP 2004022334 A), Jan. 22, 2004.

* cited by examiner

*Primary Examiner* — Venkataraman Balasubramanian
(74) *Attorney, Agent, or Firm* — Greenblum & Bernstein, P.L.C.

(57) ABSTRACT

A 1,3,5-triazine derivative represented by the formula (1):

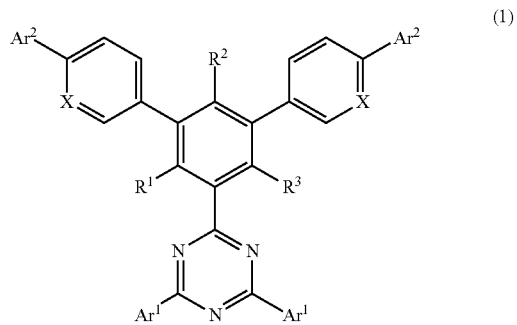

wherein $R^1$, $R^2$ and $R^3$ each independently represent a hydrogen atom or a methyl group; X represents a carbon atom or a nitrogen atom; $Ar^1$ represents a substituted or unsubstituted aromatic hydrocarbon group; $Ar^2$ represents an $C_{1-4}$ alkyl-substituted or unsubstituted aromatic 6-membered heterocyclic group having one or two nitrogen atoms, which may be a condensed ring compound. An organic electroluminescent device comprising the 1,3,5-triazine derivative exhibits low power consumption and long lifetime.

5 Claims, 1 Drawing Sheet

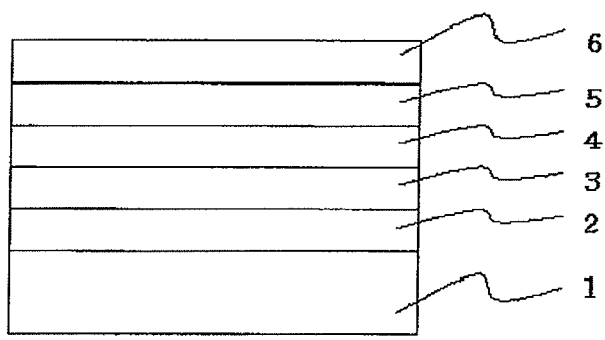

1,3,5-TRIAZINE DERIVATIVE, PROCESS FOR PRODUCING SAME, AND ORGANIC ELECTROLUMINESCENT ELEMENT COMPRISING SAME AS CONSTITUENT COMPONENT

TECHNICAL FIELD

This invention relates to a 1,3,5-triazine derivative, a process for producing the 1,3,5-triazine derivative, and an organic electroluminescent device comprising the 1,3,5-triazine derivative as a constituent. More particularly it relates to a 1,3,5-triazine derivative having a substituent such as a pyrazyl group, a pyrimidyl group, a quinoxalyl group, a quinazolyl group, a quinolyl group or an isoquinolyl group, which is useful as a constituent of an organic electroluminescent device, and a process for producing the 1,3,5-triazine derivative; and further relates to an organic electroluminescent device having at least one organic compound layer comprising the 1,3,5-triazine derivative as a constituent, which exhibits a reduced power consumption and has an enhanced lifetime.

BACKGROUND ART

An organic electroluminescent device has a multilayer structure comprising (i) a luminescent layer comprising a light emitting compound, (ii) a hole transport layer and an electron transport layer, which sandwich the luminescence layer, and (iii) an anode and a cathode, which sandwich the hole transport layer, the luminescent layer and the electron transport layer. The organic electroluminescent device utilizes light emission (fluorescence or phosphorescence) occurring at deactivation of an exciton formed by the recombination of electron with hole, which are injected in the luminescent layer.

In recent years, a wide spread attention is attracted to an organic electroluminescent device for next-generation flat panel displays. This is because, first, an electroluminescent device can be made into a thin film and be rendered light in weight; secondly, power consumption is low due to the spontaneous light emission; and thirdly, the device structure is simple and thus the production cost is low. Various methods can be adopted for the production thereof, which include, for example, vacuum deposition, spin coating, ink-jet printing, off-set printing and thermal transfer printing.

Now various mobile devices such as cell phones, mobile music devices, and personal digital assistant (PDA) are widely used. However, if mobile devices can be larger in size or more precise, organic electroluminescent devices are expected to be used in, for example, flat panel displays, lighting systems with a surface-light-emitting source, flexible paper-like displays, wearable displays and transparent see-through displays. Its use is expected to be rapidly spread.

However, an organic electroluminescent device still has many technical problems to be solved. Especially its driving voltage is high and its efficiency is low, and therefore, its power consumption is high. In addition, the high driving voltage often causes shortening of lifetime of the organic electroluminescent device.

The above-mentioned technical problems arise due to the property of the material constituting the organic electroluminescent device, especially the property of electron transport material. Many materials including triarylamine derivatives have been proposed as a hole transport material, but, only several reports are found as to the electron transport material. Tris(8-quinolinolato)-aluminum (III)(Alq) is already put in practical use as an electron transport material, but, its property is poor as compared with a hole transport material such as, for example, N,N'-bis(1-naphthyl)-N,N'-diphenyl-4,4'-biphenyl (NPD), and an organic electroluminescent material comprising the electron transport material has also poor property.

As other electron transport materials, there can be mentioned oxadiazole derivatives (patent document 1), quinoxaline derivatives (patent document 2), triazole derivatives (patent document 3), silacyclopentadiene derivatives (patent document 4), quinoline derivatives (patent document 5), benzimidazole derivatives (patent document 6) and benzothiazole derivatives (non-patent document 1). However, organic electroluminescent devices comprising these electron transport materials still have problems in practice in that their driving voltage is high, the film is readily crystallized, and their lifetime is short.

Recently, 1,3,5-triazine derivatives have been proposed as materials for organic electroluminescent devices (patent documents 7 and 8). These proposed triazine derivatives have benzoazol moieties in 2, 4 and 6 positions of the triazine ring, and thus, their chemical structures are clearly distinguished from the 1,3,5-triazine derivative of the present invention.

Use of 1,3,5-triazine derivatives for organic electroluminescent device is described in patent documents 9 to 12. These 1,3,5-triazine derivatives have two phenyl substituents in o- and p-positions or m- and p-positions. In the patent documents, 1,3,5-triazine derivatives having two phenyl substituents in o- and p-positions or m- and p-positions are described. However, 1,3,5-triazine derivatives having two phenyl substituents in 3- and 5-positions such as the 1,3,5-triazine derivatives of the present invention are not described at all.

Use of 1,3,5-triazine derivatives for organic electroluminescent device is described further in patent document 13. The 1,3,5-triazine derivatives described therein have aromatic heterocyclic substituents in all of the 2-, 4- and 6-positions of the 1,3,5-triazine derivatives, and therefore, the 1,3,5-triazine derivatives are different from the 1,3,5-triazine derivatives of the present invention.

One example of 1,3,5-triazine derivative used for organic electroluminescent device is mentioned in patent document 14 (page 27, compound No. C-8). The exemplified 1,3,5-triazine derivative has the same aromatic hydrocarbon substituents in the 2-, 4- and 6-positions of the 1,3,5-triazine derivative, therefore, it is distinguished from the 1,3,5-triazine derivatives of the present invention.

Another example of 1,3,5-triazine derivative used for organic electroluminescent device is mentioned in patent document 15 (page 8, compound No. 1). The exemplified 1,3,5-triazine derivative has the same 4-monosubstituted phenyl groups in the 2-, 4- and 6-positions of the 1,3,5-triazine derivative, therefore, it is distinguished from the 1,3,5-triazine derivatives of the present invention.

Use of 1,3,5-triazine derivatives for organic electroluminescent device is described further in patent document 16. These 1,3,5-triazine derivatives have mono-substituted phenyl groups in the 2-, 4- and 6-positions of the 1,3,5-triazine derivatives, therefore, it is distinguished from the 1,3,5-triazine derivatives of the present invention.

Use of 1,3,5-triazine derivatives for organic electroluminescent device is described further in patent document 17. The 1,3,5-triazine derivatives described therein have substituted phenyl groups in 2-, 4- and 6-positions thereof, but, the positions of substituents in each phenyl group, at which the substituents are bonded to the phenyl group, are not defined. Patent document 17 is silent, in the description thereof including working examples, on the 1,3,5-triazine derivative of the present invention, which has a 3,5-disubstituted phenyl group as one substituent at 2-position of the triazine ring, and further has two aromatic hydrocarbon groups as substituents at 4- and 6-positions of the triazine ring. Further, the 1,3,5-triazine derivative of the present invention cannot be produced by the processes described in the working examples in patent document 17.

Patent document 1: JP H6-136359 A
Patent document 2: JP H6-207169 A
Patent document 3: WO95/25097
Patent document 4: JP 2005-104986 A
Patent document 5: JP 2006-199677 A
Patent document 6: WO2004/080975
Patent document 7: JP H7-157473 A
Patent document 8: JP 2003-303689 A
Patent document 9: U.S. Pat. No. 6,057,048
Patent document 10: U.S. Pat. No. 6,229,012
Patent document 11: U.S. Pat. No. 6,225,467
Patent document 12: JP 2004-63465 A
Patent document 13: JP 2003-45662 A
Patent document 14: JP 2001-143869 A
Patent document 15: JP 2003-282270 A
Patent document 16: JP 4106974 B
Patent document 17: JP 2007-137829 A
Non-patent document 1: Applied Physics Letters, vol. 89, 063504, 2006.

DISCLOSURE OF THE INVENTION

Problems to be Solved by the Invention

An object of the present invention is to provide a 1,3,5-triazine derivative having a novel structure, which gives an organic electroluminescent device exhibiting a sufficiently reduced driving voltage and a long lifetime.

Another object of the present invention is to provide a process for producing the above-mentioned 1,3,5-triazine derivative by an industrially advantageous procedure.

A further object of the present invention is to provide an organic electroluminescent device exhibiting a sufficiently reduced driving voltage and a long lifetime.

Means for Solving the Problems

The inventors made an extensive research for solving the above-mentioned problems, and found that a specific 1,3,5-triazine derivative having a substituent such as a pyrazyl group, a pyrimidyl group, a quinoxalyl group, a quinazolyl group, a quinolyl group or an isoquinolyl group, can be formed into an amorphous thin film by any procedure of vacuum deposition and spin coating, and further that an organic electroluminescent device comprising the 1,3,5-triazine derivative as electron transport material exhibits a sufficiently reduced driving voltage and a long lifetime, as compared with the conventional organic electroluminescent devices. On the basis of these findings, the present invention has been completed.

Thus, in one aspect of the present invention, there is provided a 1,3,5-triazine derivative represented by the following general formula (1):

(1)

wherein:
$R^1$, $R^2$ and $R^3$ each independently represent a hydrogen atom or a methyl group;
X represents a carbon atom or a nitrogen atom;
$Ar^1$ represents a substituted or unsubstituted aromatic hydrocarbon group;
$Ar^2$ represents an aromatic 6-membered heterocyclic group having one or two nitrogen atoms, which may be a condensed ring compound, and may have an alkyl substituent or substituents each having 1 to 4 carbon atoms.

In another aspect of the present invention, there is provided a process for producing a 1,3,5-triazine derivative represented by the following general formula (1):

(1)

wherein:
$R^1$, $R^2$ and $R^3$ each independently represent a hydrogen atom or a methyl group;
X represents a carbon atom or a nitrogen atom;
$Ar^1$ represents a substituted or unsubstituted aromatic hydrocarbon group;
$Ar^2$ represents an aromatic 6-membered heterocyclic group having one or two nitrogen atoms, which may be a condensed ring compound, and may have an alkyl substituent or substituents each having 1 to 4 carbon atoms;
characterized by coupling a compound represented by the following general formula (2) with a compound represented by the following general formula (3) in the presence of a palladium catalyst and in the presence or absence of a base;

(2)

wherein:

X represents a carbon atom or a nitrogen atom;

$Ar^2$ represents an aromatic 6-membered heterocyclic group having one or two nitrogen atoms, which may be a condensed ring compound, and may have an alkyl substituent or substituents each having 1 to 4 carbon atoms; and M represents $ZnR^4$, $MgR^5$, $Sn(R^6)_3$ or $B(OR^7)_2$, where $R^4$ and $R^5$ independently represent a chlorine atom, a bromine atom or an iodine atom, $R^6$ represents an alkyl group having 1 to 4 carbon atoms, or a phenyl group, and the three $R^6$s may be the same or different, $R^7$ represents a hydrogen atom, an alkyl group having 1 to 4 carbon atoms, or a phenyl group, and the two $R^7$s may be the same or different, and can form a ring together with the boron atom bonded to the two $R^7$s via the respective oxygen atoms;

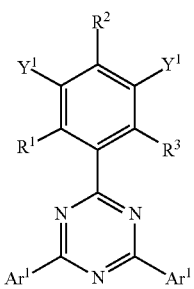

(3)

wherein:

$R^1$, $R^2$ and $R^3$ each independently represent a hydrogen atom or a methyl group;

$Ar^1$ represents a substituted or unsubstituted aromatic hydrocarbon group; and $Y^1$ represents a chlorine atom, a bromine atom, an iodine atom or a trifluoromethanesulfoxy group.

In a further aspect of the present invention, there is provided a process for producing a 1,3,5-triazine derivative represented by the following general formula (1):

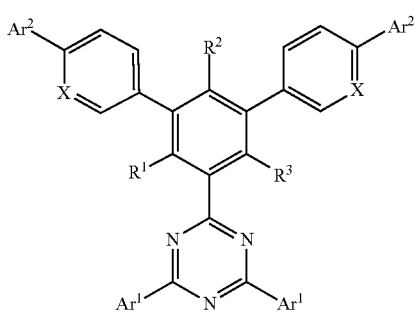

(1)

wherein:

$R^1$, $R^2$ and $R^3$ each independently represent a hydrogen atom or a methyl group;

X represents a carbon atom or a nitrogen atom;

$Ar^1$ represents a substituted or unsubstituted aromatic hydrocarbon group;

$Ar^2$ represents an aromatic 6-membered heterocyclic group having one or two nitrogen atoms, which may be a condensed ring compound, and may have an alkyl substituent or substituents each having 1 to 4 carbon atoms;

characterized by coupling a compound represented by the following general formula (4) with a compound represented by the following general formula (5) in the presence of a palladium catalyst and in the presence of a base;

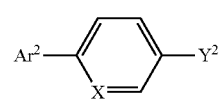

(4)

wherein:

X represents a carbon atom or a nitrogen atom;

$Ar^2$ represents an aromatic 6-membered heterocyclic group having one or two nitrogen atoms, which may be a condensed ring compound, and may have an alkyl substituent or substituents each having 1 to 4 carbon atoms; and $Y^2$ represents a chlorine atom, a bromine atom, an iodine atom or a trifluoromethanesulfoxy group.

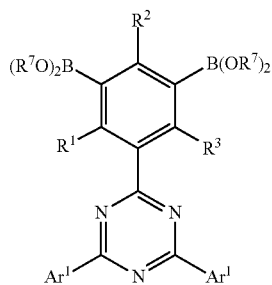

(5)

wherein:

$R^1$, $R^2$ and $R^3$ each independently represent a hydrogen atom or a methyl group;

$Ar^1$ represents a substituted or unsubstituted aromatic hydrocarbon group;

$R^7$ represents a hydrogen atom, an alkyl group having 1 to 4 carbon atoms or a phenyl group, and the two $R^7$s may be the same or different, and the two $R^7$s can form a ring together with the boron atom bonded to the two $R^7$s via the respective oxygen atoms.

In a further aspect of the present invention, there is provided an organic electroluminescent device characterized by containing as a constituent a 1,3,5-triazine derivative represented by the following general formula (1):

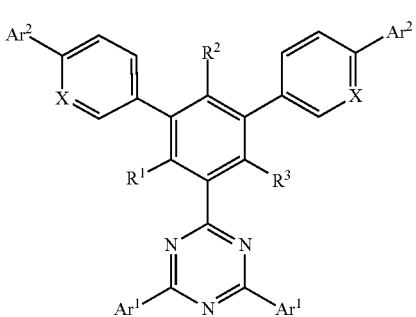

(1)

wherein:

$R^1$, $R^2$ and $R^3$ each independently represent a hydrogen atom or a methyl group;

X represents a carbon atom or a nitrogen atom;

Ar¹ represents a substituted or unsubstituted aromatic hydrocarbon group;

Ar² represents an aromatic 6-membered heterocyclic group having one or two nitrogen atoms, which may be a condensed ring compound, and may have an alkyl substituent or substituents each having 1 to 4 carbon atoms;

BRIEF DESCRIPTION OF THE DRAWINGS

FIG. 1 illustrates a schematic cross-section of an organic electroluminescent device made in the examples.

EXPLANATION OF REFERENCE NUMERALS

1. Glass substrate with transparent ITO electrode
2. Hole injection layer
3. Hole transport layer
4. Light emitting layer
5. Electron transport layer
6. Cathode layer

BEST MODE FOR CARRYING OUT THE INVENTION

The invention will now be described in detail.

In the general formula (1), $R^1$, $R^2$ and $R^3$ each independently represent a hydrogen atom or a methyl group. In view of good performance of an organic electroluminescent device, a hydrogen atom is preferable.

X represents a carbon atom or a nitrogen atom. In view of good performance of an organic electroluminescent device, a carbon atom is preferable.

Ar¹ represents a substituted or unsubstituted aromatic hydrocarbon group, which includes a substituted or unsubstituted phenyl group and a substituted or unsubstituted naphthyl group.

As specific examples of Ar¹, the following substituted or unsubstituted phenyl groups and substituted or unsubstituted naphthyl groups can be mentioned. But, Ar¹ should not be construed to be limited thereto.

The substituted or unsubstituted phenyl groups include, for example, phenyl group, p-tolyl group, m-tolyl group, o-tolyl group, 4-trifluoromethylphenyl group, 3-trifluoromethylphenyl group, 2-trifluoromethylphenyl group, 2,4-dimethylphenyl group, 3,5-dimethylphenyl group, mesityl group, 2-ethylphenyl group, 3-ethylphenyl group, 4-ethylphenyl group, 2,4-diethylphenyl group, 3,5-diethylphenyl group, 2-propylphenyl group, 3-propylphenyl group, 4-propylphenyl group, 2,4-dipropylphenyl group, 3,5-dipropylphenyl group, 2-isopropylphenyl group, 3-isopropylphenyl group, 4-isopropylphenyl group, 2,4-diisopropylphenyl group, 3,5-diisopropylphenyl group, 2-butylphenyl group, 3-butylphenyl group, 4-butylphenyl group, 2,4-dibutylphenyl group, 3,5-dibutylphenyl group, 2-tert-butylphenyl group, 3-tert-butylphenyl group, 4-tert-butylphenyl group, 2,4-di-tert-butylphenyl group, 3,5-di-tert-butylphenyl group, 4-biphenylyl group, 3-biphenylyl group, 2-biphenylyl group, 2-methylbiphenyl-4-yl group, 3-methylbiphenyl-4-yl group, 2'-methylbiphenyl-4-yl group, 4'-methylbiphenyl-4-yl group, 2,2'-dimethylbiphenyl-4-yl group, 2',4',6'-trimethylbiphenyl-4-yl group, 6-methylbiphenyl-3-yl group, 5-methylbiphenyl-3-yl group, 2'-methylbiphenyl-3-yl group, 4'-methylbiphenyl-3-yl group, 6,2'-dimethylbiphenyl-3-yl group, 2',4',6'-trimethylbiphenyl-3-yl group, 5-methylbiphenyl-2-yl group, 6-methylbiphenyl-2-yl group, 2'-methylbiphenyl-2-yl group, 4'-methylbiphenyl-2-yl group, 6,2'-dimethylbiphenyl-2-yl group, 2',4',6'-trimethylbiphenyl-2-yl group, 2-trifluoromethylbiphenyl-4-yl group, 3-trifluoromethylbiphenyl-4-yl group, 2'-trifluoromethylbiphenyl-4-yl group, 4'-trifluoromethylbiphenyl-4-yl group, 6-trifluoromethylbiphenyl-3-yl group, 5-trifluoromethylbiphenyl-3-yl group, 2'-trifluoromethylbiphenyl-3-yl group, 4'-trifluoromethylbiphenyl-3-yl group, 5-trifluoromethylbiphenyl-2-yl group, 6-trifluoromethylbiphenyl-2-yl group, 2'-trifluoromethylbiphenyl-2-yl group, 4'-trifluoromethylbiphenyl-2-yl group, 3-ethylbiphenyl-4-yl group, 4'-ethylbiphenyl-4-yl group, 2',4',6'-triethylbiphenyl-4-yl group, 6-ethylbiphenyl-3-yl group, 4'-ethylbiphenyl-3-yl group, 5-ethylbiphenyl-2-yl group, 4'-ethylbiphenyl-2-yl group, 2',4',6'-triethylbiphenyl-2-yl group, 3-propylbiphenyl-4-yl group, 4'-propylbiphenyl-4-yl group, 2',4',6'-tripropylbiphenyl-4-yl group, 6-propylbiphenyl-3-yl group, 4'-propylbiphenyl-3-yl group, 5-propylbiphenyl-2-yl group, 4'-propylbiphenyl-2-yl group, 2',4',6'-tripropylbiphenyl-2-yl group, 3-isopropylbiphenyl-4-yl group, 4'-isopropylbiphenyl-4-yl group, 2',4',6'-triisopropylbiphenyl-4-yl group, 6-isopropylbiphenyl-3-yl group, 4'-isopropylbiphenyl-3-yl group, 5-isopropylbiphenyl-2-yl group, 4'-isopropylbiphenyl-2-yl group, 2',4',6'-triisopropylbiphenyl-2-yl group, 3-butylbiphenyl-4-yl group, 4'-butylbiphenyl-4-yl group, 2',4',6'-tributylbiphenyl-4-yl group, 6-butylbiphenyl-3-yl group, 4'-butylbiphenyl-3-yl group, 5-butylbiphenyl-2-yl group, 4'-butylbiphenyl-2-yl group, 2',4',6'-tributylbiphenyl-2-yl group, 3-tert-butylbiphenyl-4-yl group, 4'-tert-butylbiphenyl-4-yl group, 2',4',6'-tri-tert-butylbiphenyl-4-yl group, 6'-tert-butylbiphenyl-3-yl group, 4'-tert-butylbiphenyl-3-yl group, 5-tert-butylbiphenyl-2-yl group, 4'-tert-butylbiphenyl-2-yl group and 2',4',6'-tri-tert-butylbiphenyl-2-yl group.

Of these, phenyl group, p-tolyl group, m-tolyl group, o-tolyl group, 4-butylphenyl group, 4-tert-butylphenyl group, 4-biphenylyl group and 3-biphenylyl group are preferable in view of the performance thereof as a material for an organic electroluminescent device. Phenyl group, p-tolyl group and 3-biphenylyl group are especially preferable in view of ease in synthesis.

The substituted or unsubstituted naphthyl groups include, for example, 1-naphthyl group, 4-methylnaphthalen-1-yl group, 4-trifluoromethylnaphthalen-1-yl group, 4-ethylnaphthalen-1-yl group, 4-propylnaphthalen-1-yl group, 4-butylnaphthalen-1-yl group, 4-tert-butylnaphthalen-1-yl group, 5-methylnaphthalen-1-yl group, 5-trifluoromethylnaphthalen-1-yl group, 5-ethylnaphthalen-1-yl group, 5-propylnaphthalen-1-yl group, 5-butylnaphthalen-1-yl group, 5-tert-butylnaphthalen-1-yl group, 2-naphthyl group, 6-methylnaphthalen-2-yl group, 6-trifluoromethylnaphthalen-2-yl group, 6-ethylnaphthalen-2-yl group, 6-propylnaphthalen-2-yl group, 6-butylnaphthalen-2-yl group, 6-tert-butylnaphthalen-2-yl group, 7-methylnaphthalen-2-yl group, 7-trifluoromethylnaphthalen-2-yl group, 7-ethylnaphthalen-2-yl group, 7-propylnaphthalen-2-yl group, 7-butylnaphthalen-2-yl group and 7-tert-butylnaphthalen-2-yl group.

Of these, 1-naphthyl group, 4-methylnaphthalene-1-yl group, 4-tert-butylnaphthalen-1-yl group, 5-methylnaphthalen-1-yl group, 5-tert-butylnaphthalen-1-yl group, 2-naphthyl group, 6-methylnaphthalen-2-yl group, 6-tert-butylnaphthalen-2-yl group, 7-methylnaphthalene-2-yl group and 7-tert-butylnaphthalen-2-yl group are preferable in view of the performance thereof as a material for an organic electroluminescent device. 2-Naphthyl group is especially preferable because of ease in synthesis.

In the general formula (1), Ar² represents an aromatic 6-membered heterocyclic group having one or two nitrogen atoms, which may be a condensed ring compound, and may have an alkyl substituent or substituents each having 1 to 4 carbon atoms. Such group is not particularly limited, and, includes, for example, a pyrazyl group which may have an alkyl substituent or substituents each having 1 to 4 carbon atoms, a 2-pyrimidyl group which may have an alkyl substituent or substituents each having 1 to 4 carbon atoms, a 2-quinoxalyl group which may have an alkyl substituent or substituents each having 1 to 4 carbon atoms, a quinazolyl group which may have an alkyl substituent or substituents each having 1 to 4 carbon atoms, a quinolyl group which may have an alkyl substituent or substituents each having 1 to 4 carbon atoms, and an isoquinolyl group which may have an alkyl substituent or substituents each having 1 to 4 carbon atoms.

As specific examples of Ar², the following $C_{1-4}$ alkyl-substituted or unsubstituted aromatic 6-membered heterocyclic groups can be mentioned. But, Ar² should not be construed to be limited thereto.

The pyrazyl group, which may have an alkyl substituent or substituents each having 1 to 4 carbon atoms, includes, for example, 2-pyrazyl group, 3-methylpyrazin-2-yl group, 5-methylpyrazin-2-yl group, 6-methylpyrazin-2-yl group, 3-tert-butylpyrazin-2-yl group, 5-tert-butylpyrazin-2-yl group, 6-tert-butylpyrazin-2-yl group and 5,6-dimethylpyrazin-2-yl group.

Of these, 2-pyrazyl group and 5,6-dimethylpyrazin-2-yl group are preferable in view of the performance thereof as a material for an organic electroluminescent device. 2-Pyrazyl group is especially preferable because of ease in synthesis.

The 2-pyrimidyl group which may have an alkyl substituent or substituents each having 1 to 4 carbon atoms, includes, for example, 2-pyrimidyl group, 4,6-dimethylpyrimidin-2-yl group and 4,6-di(tert-butyl)pyrimidin-2-yl group.

Of these, 2-pyrimidyl group and 4,6-dimethylpyrimidin-2-yl group are preferable in view of the performance thereof as a material for an organic electroluminescent device. 2-Pyrimidyl group is especially preferable because of ease in synthesis.

The 2-quinoxalyl group, which may have an alkyl substituent or substituents each having 1 to 4 carbon atoms, includes, for example, 2-quinoxalyl group, 3-methylquinoxalin-2-yl group, 5-methylquinoxalin-2-yl group, 6-methylquinoxalin-2-yl group, 7-methylquinoxalin-2-yl group, 8-methylquinoxalin-2-yl group, 5,7-dimethylquinoxalin-2-yl group, 5,6,7,8-tetramethylquinoxalin-2-yl group, 3-tert-butylquinoxalin-2-yl group and 6-tert-butylquinoxalin-2-yl group.

Of these, 2-quinoxalyl group, 3-methylquinoxalin-2-yl group and 3-tert-butylquinoxalin-2-yl group are preferable in view of the performance thereof as a material for an organic electroluminescent device. 2-Quinoxalyl group is especially preferable because of ease in synthesis.

The quinazolyl group, which may have an alkyl substituent or substituents each having 1 to 4 carbon atoms, includes, for example, 2-quinazolyl group, 4-methylquinazolin-2-yl group, 5-methylquinazolin-2-yl group, 6-methylquinazolin-2-yl group, 7-methylquinazolin-2-yl group, 8-methylquinazolin-2-yl group, 5,7-dimethylquinazolin-2-yl group, 5,6,7,8-tetramethylquinazolin-2-yl group, 4-tert-butylquinazolin-2-yl group and 6-tert-butylquinazolin-2-yl group.

Of these, 2-quinazolyl group, 4-methylquinazolin-2-yl group and 4-tert-butylquinazolin-2-yl group are preferable in view of the performance thereof as a material for an organic electroluminescent device. 2-Quinazolyl group is especially preferable because of ease in synthesis.

The quinolyl group, which may have an alkyl substituent or substituents each having 1 to 4 carbon atoms, includes, for example, 2-quinolyl group, 3-quinolyl group, 4-quinolyl group, 3-methylquinolin-2-yl group, 4-methylquinolin-2-yl group, 5-methylquinolin-2-yl group, 6-methylquinolin-2-yl group, 7-methylquinolin-2-yl group, 8-methylquinolin-2-yl group, 5,8-dimethylquinolin-2-yl group, 5,6,7,8-tetramethylquinolin-2-yl group, 4-tert-butylquinolin-2-yl group and 6-tert-butylquinolin-2-yl group.

Of these, 2-quinolyl group, 3-methylquinolin-2-yl group and 4-tert-butylquinolin-2-yl group are preferable in view of the performance thereof as a material for an organic electroluminescent device. 2-Quinolyl group is especially preferable because of ease in synthesis.

The isoquinolyl group, which may have an alkyl substituent or substituents each having 1 to 4 carbon atoms, includes, for example, 1-isoquinolyl group, 3-isoquinolyl group, 4-isoquinolyl group, 3-methylisoquinolyn-1-yl group, 4-methylisoquinolyn-1-yl group, 5-methylisoquinolyn-1-yl group, 6-methylisoquinolyn-1-yl group, 7-methylisoquinolyn-1-yl group, 8-methylisoquinolyn-1-yl group, 1,3-dimethylisoquinolyn-4-yl group, 5,8-dimethylisoquinolyn-1-yl group, 5,6,7,8-tetramethylisoquinolyn-1-yl group, 1-methylisoquinolyn-3-yl group, 4-methylisoquinolyn-3-yl group, 5-methylisoquinolyn-3-yl group, 6-methylisoquinolyn-3-yl group, 7-methylisoquinolyn-3-yl group, 8-methylisoquinolyn-3-yl group, 5,8-dimethylisoquinolyn-3-yl group, 5,6,7,8-tetramethylisoquinolyn-3-yl group, 1-methylisoquinolyn-4-yl group, 3-methylisoquinolyn-4-yl group, 5-methylisoquinolyn-4-yl group, 6-methylisoquinolyn-4-yl group, 7-methylisoquinolyn-4-yl group, 8-methylisoquinolyn-4-yl group, 5,8-dimethylisoquinolyn-4-yl group, 5,6,7,8-tetramethylisoquinolyn-4-yl group, 3-tert-butylisoquinolyn-1-yl group, 4-tert-butylisoquinolyn-1-yl group, 6-tert-butylisoquinolyn-1-yl group, 7-tert-butylisoquinolyn-1-yl group, 1-tert-butylisoquinolyn-yl group, 4-tert-butylisoquinolyn-3-yl group, 6-tert-butylisoquinolyn-3-yl group, 7-tert-butylisoquinolyn-3-yl group, 1-tert-butylisoquinolyn-4-yl group, 3-tert-butylisoquinolyn-4-yl group, 6-tert-butylisoquinolyn-4-yl group and 7-tert-butylisoquinolyn-4-yl group.

Of these, 1-isoquinolyl group, 3-isoquinolyl group, 4-isoquinolyl group and 1,3-dimethylisoquinolin-4-yl group are preferable in view of the performance thereof as a material for an organic electroluminescent device. 1-Isoquinolyl group and 4-isoquinolyl group are especially preferable because of ease in synthesis.

The process for producing the compound represented by the formula (1) will now be described.

The process for producing the compound of formula (1) includes a process comprising coupling the compound represented by the formula (2) with the compound represented by the formula (3) (which process is hereinafter referred to "first production process" when appropriate), and a process comprising coupling the compound represented by the formula (4) with the compound represented by the formula (5) (which process is hereinafter referred to "second production process" when appropriate).

As preferable examples of the compound of formula (2) used in the first production process, there can be mentioned those which have the following skeletal structures (I) through (XXXIII), but the compound of formula (2) is not limited thereto.

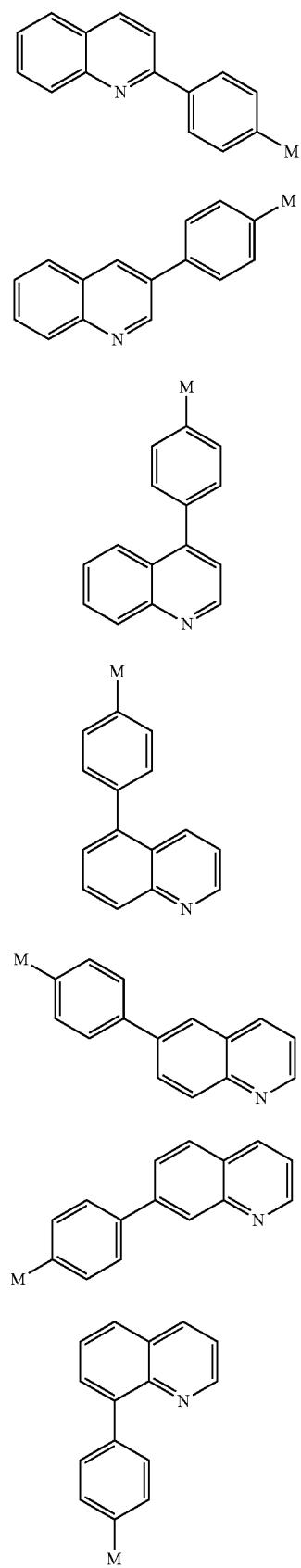
(I)
(II)
(III)
(IV)
(V)
(VI)
(VII)
-continued
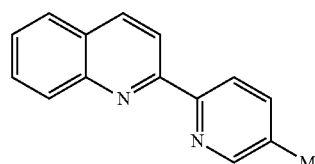
(VIII)
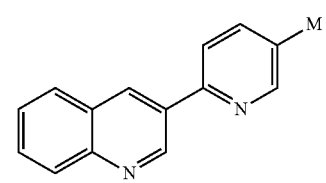
(IX)
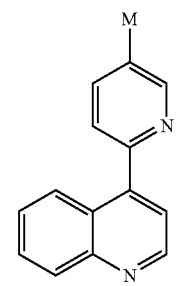
(X)
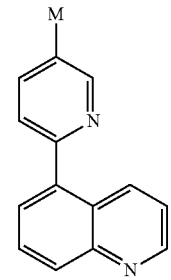
(XI)
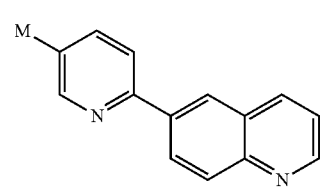
(XII)
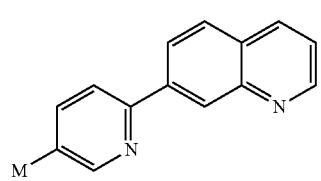
(XIII)
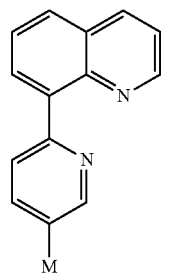
(XIV)

-continued (XV)

(XVI)

(XVII)

(XVIII)

(XIX)

(XX)

(XXI)

(XXII)

(XXIII)

(XXIV)

(XXV)

(XXVI)

-continued (XXVII)

(XXVIII)

(XXIX)

(XXX)

(XXXI)

(XXXII)

(XXXIII)

As specific examples of $ZnR^4$ and $MgR^5$ which are represented by M in formula (2), there can be mentioned ZnCl, ZnBr, ZnI, MgCl, MgBr and MgI. Of these, ZnCl is preferable in view of the reaction yield. ZnCl coordinated with tetramethylethylenediamine (TMEDA) is especially preferable.

As specific examples of Sn $(R^6)_3$ represented by M in formula (2), there can be mentioned $SnMe_3$ and $SnBu_3$.

As specific examples of $B(OR^7)_2$ represented by M in formula (2), there can be mentioned $B(OH)_2$, $B(OMe)_2$, $B(O(iso-Pr))_2$ and $B(OBu)_2$.

In the formula $B(OR^7)_2$ represented by M, when the two $R^7$s form a ring together with the boron atom bonded to the two $R^7$s via the respective oxygen atoms, as examples of such B $(OR^7)_2$, the following groups (XXXIV) through (XL) are mentioned. Of these, the group represented (XXXV) is preferable in view of the reaction yield.

(XXXIV)

(XXXV)

(XXXVI)

(XXXVII)

(XXXVIII)

(XXXIX)

(XL)

In the general formula (3), $Y^1$ represents a chlorine atom, a bromine atom, an iodine atom or a trifluoromethanesulfoxy group. Of these, a bromine atom is preferable in view of the reaction yield and the selectivity.

As preferable examples of the compound represented by the general formula (4) used in the second production process, there can be mentioned those which have the following skeletal structures (XLI) through (LXXIII), but the compound of formula (4) is not limited thereto.

(XLI)

(XLII)

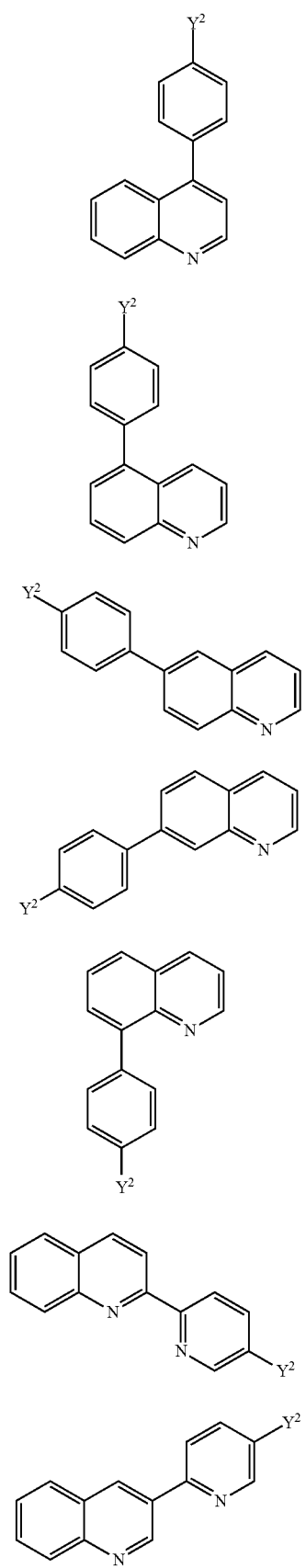
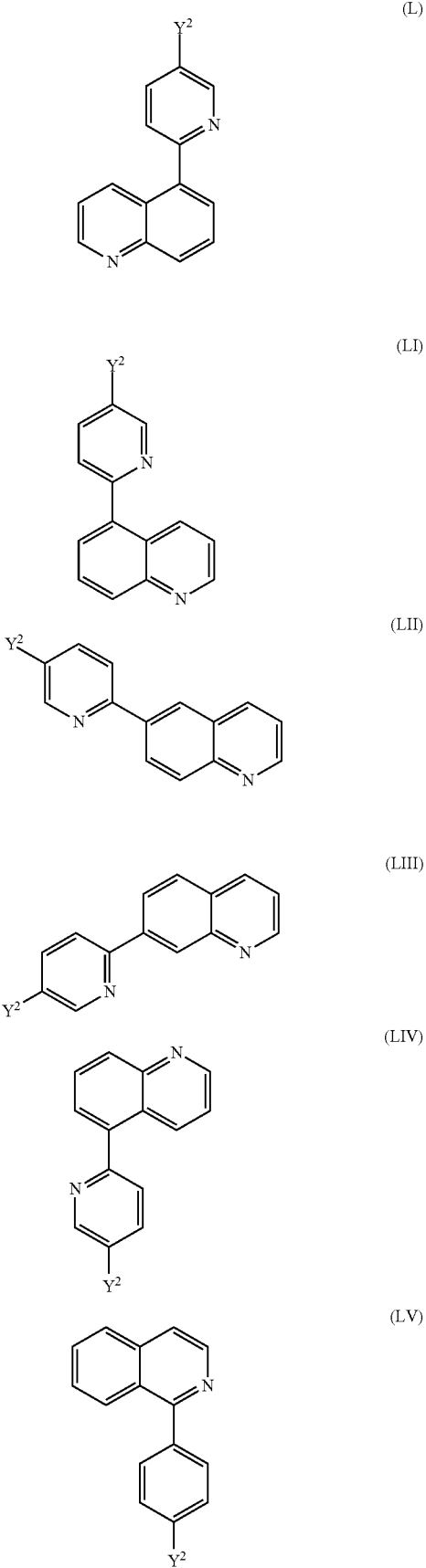

-continued
(LVI)
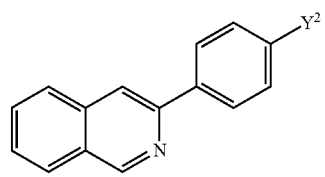
(LVII)
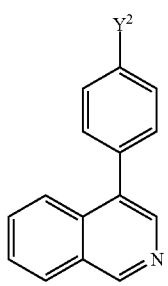
(LVIII)
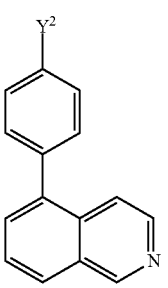
(LIX)
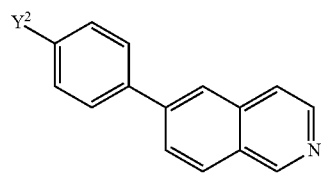
(LX)
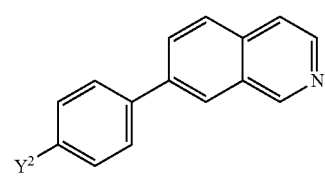
(LXI)
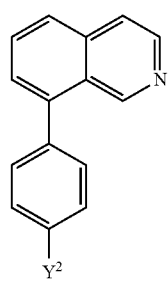
-continued
(LXII)
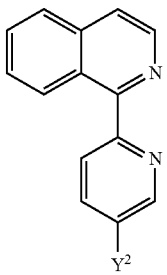
(LXIII)
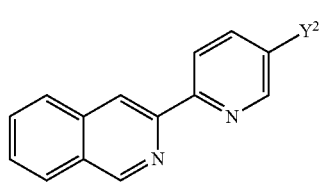
(LXIV)
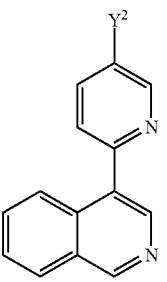
(LXV)
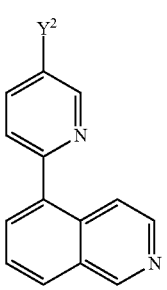
(LXVI)
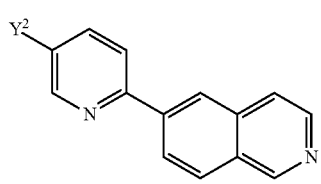
(LXVII)
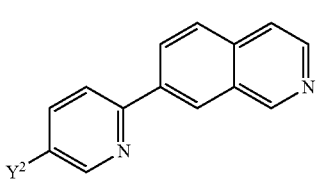

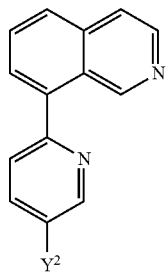

(LXVIII)

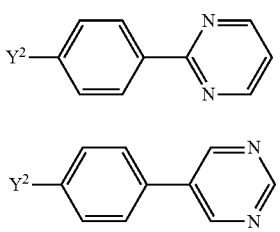

(LXIX)

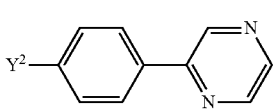

(LXX)

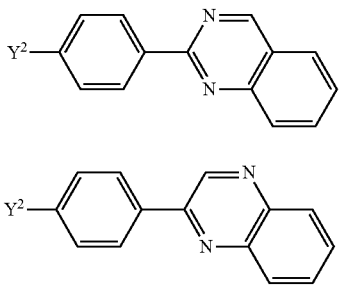

(LXXI)

(LXXII)

(LXXIII)

In the above-recited skeletal structures (XLI) through (LXXIII), $Y^2$ represents a chlorine atom, a bromine atom, an iodine atom or a trifluoromethanesulfoxy group. Of these, a bromine atom is preferable in view of the reaction yield and the selectivity.

The first production process for producing the 1,3,5-triazine derivative of formula (1) according to the present invention involves the following reaction scheme.

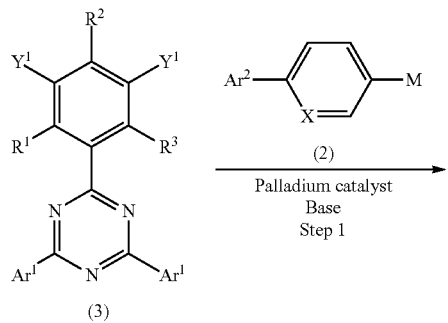

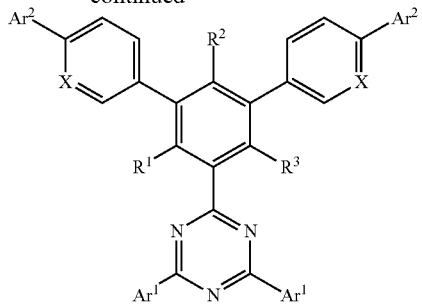

(1)

In the formulae (1), (2) and (3), $R^1$, $R^2$ and $R^3$ each independently represent a hydrogen atom or a methyl group; $Ar^1$ represents a substituted or unsubstituted aromatic hydrocarbon group; and $Ar^2$ represents an aromatic 6-membered heterocyclic group having one or two nitrogen atoms, which may be a condensed ring compound, and may have an alkyl substituent or substituents each having 1 to 4 carbon atoms. X represents a carbon atom or a nitrogen atom. $Y^1$ represents a chlorine atom, a bromine atom, an iodine atom or a trifluoromethanesulfoxy group. M represents $ZnR^4$, $MgR^5$, $Sn(R^6)_3$ or $B(OR^7)_2$, where $R^4$ and $R^5$ independently represent a chlorine atom, a bromine atom or an iodine atom, $R^6$ represents an alkyl group having 1 to 4 carbon atoms, or a phenyl group, and the three $R^6$s may be the same or different; $R^7$ represents a hydrogen atom, an alkyl group having 1 to 4 carbon atoms, or a phenyl group, and the two $R^7$s may be the same or different, and the two $R^7$s can form a ring together with the boron atom bonded to the two $R^7$s via the respective oxygen atoms.

Step 1 in the first production process comprises a step of coupling the compound of formula (2) with a compound of formula (3) in the presence of a palladium catalyst and in the presence or absence of a base to produce the 1,3,5-triazine derivative of formula (1) according to the present invention. This coupling reaction can be effected by adopting conventional reaction conditions and catalyst, which are adopted in the conventional coupling reactions such as, for example, Suzuki-Miyaura reaction, Negishi reaction, Tamao-Kumada reaction and Stille reaction. The target compound can be obtained with a high yield by adopting such reaction conditions and catalyst.

The palladium catalyst used in the step 1 includes, for example, palladium salts such as palladium chloride, palladium acetate, palladium trifluoroacetate and palladium nitrate; and complex compounds such as π-allylpalladium chloride dimmer, palladium acetylacetonate, tris(dibenzylideneacetone)-dipalladium, dichlorobis(triphenylphosphine)palladium, tetrakis(triphenylphosphine)palladium and dichloro[1,1'-bis(diphenylphosphino)ferrocene]palladium.

Of these, palladium chloride, palladium acetate, tris(dibenzylideneacetone)dipalladium, dichlorobis(triphenylphosphine)palladium and tetrakis(triphenylphosphine)palladium are preferable in view of the ease in availability and the reaction yield. Palladium complex compounds having a tertiary phosphine as a ligand are especially preferable because of high reaction yield.

The palladium complex compounds having a tertiary phosphine as a ligand can also be prepared in a reaction system comprising a palladium catalyst or a palladium complex compound, and a tertiary phosphine added therein.

As specific examples of the tertiary phosphine used, there can be mentioned triphenylphosphine, trimethylphosphine, tributylphosphine, tri(tert-butyl)phosphine, tricyclohexylphosphine, tert-butyldiphenylphosphine, 9,9-dimethyl-4,5-bis(diphenylphosphino)xanthene, 2-(diphenylphosphino)-2'-(N,N-dimethylamino)biphenyl, 2-(di-tert-butylphosphino)biphenyl, 2-(dicyclohexylphosphino)-biphenyl, bis(diphenylphosphino)methane, 1,2-bis(diphenylphosphino)ethane, 1,3-bis(diphenylphosphino)-propane, 1,4-bis(diphenylphosphino)butane, 1,1'-bis(diphenylphosphino)ferrocene, tri-(2-furyl)phosphine, tri-(o-tolyl)phosphine, tris(2,5-xylyl)phosphine, (±)-2,2'-bis(diphenylphosphino)-1,1'-binaphthyl and 2-dicyclohexylphosphino-2',4',6'-triisopropylbiphenyl.

Of these, triphenylphosphine, tri(tert-butyl)phosphine, 2-(di-tert-butylphosphino) biphenyl, 1,1'-bis(diphenylphosphino) ferrocene and 2-dicyclohexylphosphino-2',4',6'-triisopropylbiphenyl are preferable in view of ease in availability and high reaction yield.

The molar ratio of the palladium catalyst to the compound of formula (3), which are used in the step 1, is preferably in the range of 1:200 to 1:2, and more preferably 1:100 to 1:10 because of high reaction yield. The molar ratio of the tertiary phosphine to the palladium salt or the complex compound, which are used in the step 1, is preferably in the range of 1:10 to 10:1, and more preferably 1:2 to 5:1 because of high reaction yield.

The base used in the step 1 includes, for example, sodium hydroxide, potassium hydroxide, sodium carbonate, potassium carbonate, lithium carbonate, cesium carbonate, potassium phosphate, sodium phosphate, sodium fluoride, potassium fluoride and cesium fluoride. Of these, cesium carbonate is preferable because of high reaction yield. The molar ratio of the base to the compound of formula (2) is preferably in the range of 1:2 to 10:1, and more preferably 1:1 to 3:1 because of high reaction yield.

The molar ratio of the compound of formula (2) to the compound of formula (3), which are used in the step 1, is preferably in the range of 1:1 to 5:1, and more preferably 2:1 to 3:1 because of high reaction yield.

The step 1 can be effected in a reaction medium. The reaction medium used in the step 1 includes, for example, water, dimethylsulfoxide, dimethylformamide, tetrahydrofuran, toluene, benzene, diethyl ether and xylene. These reaction mediums may be used either alone or in combination. Of these, tetrahydrofuran is preferable because of high reaction yield.

The reaction in the step 1 can be effected at a temperature appropriately chosen in a range of 0° C. to 150° C. A temperature of 50° C. to 120° C. is especially preferable because of high reaction yield.

The compound of formula (1), produced by the step 1, can be treated by the conventional procedure. If desired, the produced compound is purified by, for example, recrystallization, column chromatography or sublimation.

The production process of the compound of formula (2), used as a starting material in the step 1 in the first production process for producing the 1,3,5-triazine derivative of formula (1) according to the present invention, will now be described.

The compound of formula (2) can be produced through the reaction schemes in the following step 2 and step 3, or through the reaction scheme in the following step 4.

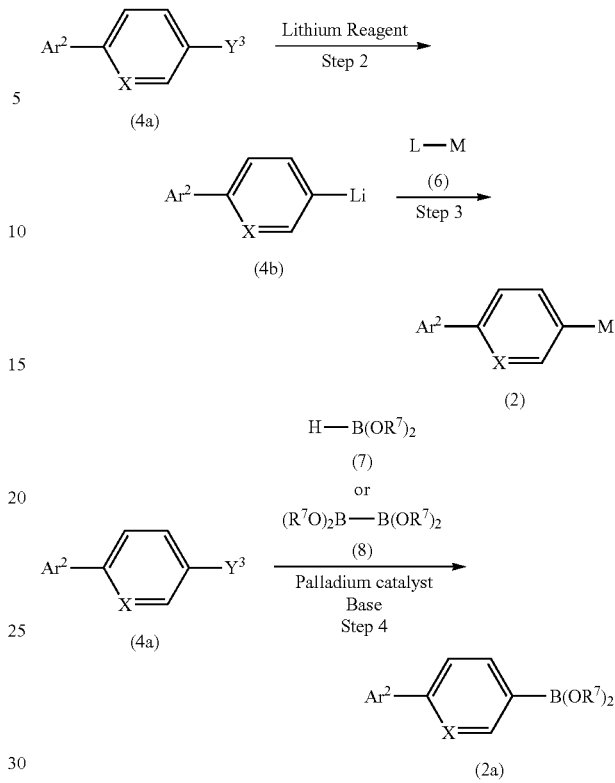

In the formulae (4a), (4b), (2) and (2a), $Ar^2$ represents an aromatic 6-membered heterocyclic group having one or two nitrogen atoms, which may be a condensed ring compound, and may have an alkyl substituent or substituents each having 1 to 4 carbon atoms. X represents a carbon atom or a nitrogen atom. $Y^3$ represents a chlorine atom, a bromine atom, an iodine atom or a trifluoromethanesulfoxy group. L represents a leaving group. M represents $ZnR^4$, $MgR^5$, $Sn(R^6)_3$ or $B(OR^7)_2$, where $R^4$ and $R^5$ independently represent a chlorine atom, a bromine atom or an iodine atom; $R^6$ represents an alkyl group having 1 to 4 carbon atoms, or a phenyl group, and the three $R^6$s may be the same or different; and $R^7$ represents a hydrogen atom, an alkyl group having 1 to 4 carbon atoms, or a phenyl group, and the two $R^7$s may be the same or different, and the two $R^7$s can form a ring together with the boron atom bonded to the two $R^7$s via the respective oxygen atoms.

The step 2 is a step of allowing a compound of the general formula (4a) to react with a lithium reagent to give a lithium compound of the general formula (4b). The lithium compound of formula (4b) produced in the step (2) can be isolated after the reaction, or used directly for the step 3 without isolation.

$Y^3$ in the compound of formula (4a) represents a chlorine atom, a bromine atom, an iodine atom or a trifluoromethanesulfoxy group. Of these, a bromine atom is preferable because of high reaction yield.

The compound of formula (4a) can be easily prepared by the conventional coupling reaction using a metal catalyst, as described in J. Tsuji: Palladium Reagents and Catalysts, John Wiley & Sons, 2004.

As preferable examples of the lithium reagent used in the step 2, butyllithium and tert-butyllithium are mentioned. The molar ratio of the lithium reagent to the compound of formula (4a) is preferably in the range of 1:1 to 5:1, and more preferably 1:1 to 3:1 because of high reaction yield.

The step 2 can be effected in a reaction medium. The reaction medium used in the step 2 includes, for example, tetrahydrofuran, toluene, benzene, diethyl ether and xylene. These reaction mediums may be used either alone or in combination. Of these, tetrahydrofuran is preferable because of high reaction yield.

The reaction in the step 2 can be effected at a temperature appropriately chosen in a range of −150° C. to −20° C. A temperature of −100° C. to −60° C. is especially preferable because of high yield.

The step 3 is a step of allowing the lithium compound of formula (4b) to react with a coupling reagent of formula (6) to give the compound of formula (2), used as a starting material for the step 1. The compound of formula (2) produced in the step 3 may be isolated after the reaction, or used for the step 1 without isolation.

As specific examples of the reagent for coupling (6) used in the step 3, there can be mentioned dichloro(tetramethylethylenediamine) zinc(II), zinc chloride, zinc bromide, zinc iodide, trimethyltin chloride, tributyltin chloride, trimethyl borate, triisopropyl borate, (2,3-dimethylbutane-2,3-dioxy)methoxyborane, (2,3-dimethylbutane-2,3-dioxy)isopropoxyborane and 1,3-propanedioxyborane. Of these, dichloro(tetramethyl-ethylenediamine)zinc(II), trimethyl borate, triisopropyl borate and (2,3-dimethylbutane-2,3-dioxy)isopropoxyborane are preferable in view of ease in handling. Dichloro(tetramethyl-ethylenediamine)zinc(II) is especially preferable because it further gives high reaction yield.

The leaving group represented by L includes, for example, Cl, Br, I, MeO and iso-PrO.

The molar ratio of the coupling reagent (6) to the compound of formula (4b) is preferably in the range of 1:1 to 10:1, and more preferably 1.5:1 to 3:1 because of high reaction yield.

The reaction in the step 3 can be effected at a temperature appropriately chosen in a range of −150° C. to 50° C. A temperature of −100° C. to 30° C. is especially preferable because of high reaction yield.

The step 4 is a step of allowing the compound of formula (4a) to react with a borane compound represented by the formula (7) or a diboron compound represented by the general formula (8) in the presence of a base and a palladium catalyst to give a compound of the general formula (2a), used in the step 1. This reaction can be effected with a high reaction yield of the target compound by adopting reaction conditions and catalysts, which are described in The Journal of Organic Chemistry, vol. 60, 7508-7510, 1995, or The Journal of Organic Chemistry, vol. 65, 164-168, 2000.

The molar ratio of the palladium catalyst to the compound of formula (4a) is preferably in the range of 1:200 to 1:2, and more preferably 1:50 to 1:10 because of high reaction yield.

The compound of formula (2a) produced can be isolated after the reaction, or used directly for the step 1 without isolation.

As examples of the palladium catalyst used in the step 4, those which are recited as examples thereof used in the step 1 are mentioned. In view of the ease in availability and the reaction yield, palladium chloride, palladium acetate, tris(dibenzylideneacetone)dipalladium, dichlorobis(triphenylphosphine)palladium, tetrakis(triphenylphosphine)palladium and dichloro[1,1'-bis(diphenylphosphino)ferrocene]palladium are preferable.

Of these, palladium complex compounds having a tertiary phosphine as a ligand are especially preferable because of high reaction yield. The palladium complex compounds having a tertiary phosphine as a ligand can also be prepared in a reaction system comprising a palladium salt or a palladium complex compound, and a tertiary phosphine added therein.

As specific examples of the tertiary phosphine used, those which are recited as examples thereof used in the step 1 are mentioned. In view of the ease in availability and high reaction yield, triphenylphosphine and 1,1'-bis(diphenylphosphino)-ferrocene are preferable.

The molar ratio of the tertiary phosphine to the palladium salt or the palladium complex compound is preferably in the range of 1:10 to 10:1, and more preferably 1:2 to 5:1 because of high reaction yield.

As examples of the base used in the step 4, those which are recited as examples thereof used in the step 1 are mentioned. In view of high reaction yield, potassium carbonate and cesium carbonate are preferable. The molar ratio of the base to the compound of formula (4a) is preferably in the range of 1:2 to 10:1, and more preferably 1:1 to 3:1 because of high reaction yield.

The molar ratio of the borane compound of formula (7) or the diboron compound of formula (8) to the compound of formula (4a) is preferably in the range of 1:1 to 5:1, and more preferably 1:1 to 3:1 because of high reaction yield.

The step 4 can be effected in a reaction medium. The reaction medium used includes, for example, dimethylsulfoxide, tetrahydrofuran, toluene, benzene, diethyl ether and xylene. These reaction mediums may be used either alone or in combination. Of these, tetrahydrofuran and dimethylsulfoxide are preferable because of high reaction yield.

The reaction in the step 4 can be effected at a temperature appropriately chosen in a range of 0° C. to 150° C. A temperature of 50° C. to 120° C. is especially preferable because of high reaction yield.

The compound of formula (2a), produced by the step 4, can be treated by the conventional procedure. If desired, the produced compound is purified by, for example, recrystallization, column chromatography or sublimation.

The compound represented by the general formula (3) can be produced by the method described in, for example, Japanese Unexamined Patent Publication 2006-62962.

The second production process for producing the 1,3,5-triazine derivative of the present invention involves the following reaction scheme.

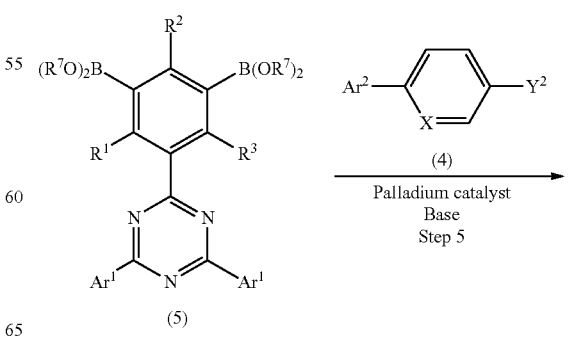

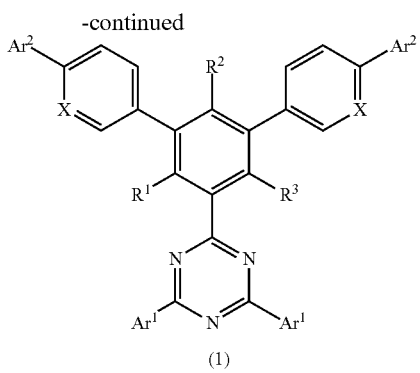

(1)

In the general formulae (5), (4) and (1), $R^1$, $R^2$ and $R^3$ each independently represent a hydrogen atom or a methyl group. $Ar^1$ represents a substituted or unsubstituted aromatic hydrocarbon group. $Ar^2$ represents an aromatic 6-membered heterocyclic group having one or two nitrogen atoms, which may be a condensed ring compound, and may have an alkyl substituent or substituents each having 1 to 4 carbon atoms. X represents a carbon atom or a nitrogen atom. $Y^2$ represents a chlorine atom, a bromine atom, an iodine atom or a trifluoromethanesulfoxy group. $R^7$ represents a hydrogen atom, an alkyl group having 1 to 4 carbon atoms or a phenyl group, and two $R^7$s may be the same or different, and the two $R^7$s can form a ring together with the boron atom bonded to the two $R^7$s via the respective oxygen atoms.

The step 5 comprises a step of allowing the compound of formula (5) to react with a compound of formula (4) in the presence of a base and a palladium catalyst to produce the 1,3,5-triazine derivative of formula (1) according to the present invention. This coupling reaction can be effected by adopting reaction conditions and catalyst, which are adopted in the conventional coupling reactions such as, for example, Suzuki-Miyaura reaction. The target compound can be obtained with a high yield by adopting such reaction conditions and catalyst.

The molar ratio of the palladium catalyst to the compound of formula (5) is preferably in the range of 1:200 to 1:2, and more preferably 1:100 to 1:10 because of high reaction yield.

As examples of the palladium catalyst used in the step 5, those which are recited as examples thereof used in the step 1 are mentioned. In view of ease in availability and high reaction yield, palladium chloride, palladium acetate, tris(dibenzylideneacetone)dipalladium, dichlorobis(triphenylphosphine)palladium and tetrakis(triphenylphosphine)palladium are preferable.

Of these, palladium complex compounds having a tertiary phosphine as a ligand are especially preferable because of high reaction yield. The palladium complex compounds having a tertiary phosphine as a ligand can also be prepared in a reaction system comprising a palladium salt or a palladium complex compound, and a tertiary phosphine added therein.

As specific examples of the tertiary phosphine used, those which are recited as examples thereof used in the step 1 are mentioned. In view of the ease in availability and high reaction yield, triphenylphosphine, tri(tert-butyl)phosphine, 2-(di-tert-butylphosphino)biphenyl and 2-dicyclohexylphosphino-2',4',6'-triisopropylbiphenyl are preferable.

The molar ratio of the tertiary phosphine to the palladium salt or the palladium complex compound is preferably in the range of 1:10 to 10:1, and more preferably 1:2 to 5:1 because of high reaction yield.

As examples of the base used in the step 5, those which are recited as examples thereof used in the step 1 are mentioned. In view of high reaction yield, cesium carbonate is especially preferable. The molar ratio of the base to the compound of formula (4) is preferably in the range of 1:2 to 10:1, and more preferably 1:1 to 3:1 because of high reaction yield.

The molar ratio of the compound of formula (4) to the compound of formula (5) is preferably in the range of 2:1 to 5:1, and more preferably 2:1 to 3:1 because of high reaction yield.

The step 5 can be effected in a reaction medium. The reaction medium used in the step 5 includes, for example, water, dimethylsulfoxide, dimethylforamide, tetrahydrofuran, toluene, benzene, diethyl ether and xylene. These reaction mediums may be used either alone or in combination. Of these, tetrahydrofuran is preferable because of high reaction yield.

The reaction in the step 5 can be effected at a temperature appropriately chosen in a range of 0° C. to 150° C. A temperature of 50° C. to 120° C. is especially preferable because of high reaction yield.

The compound of formula (1), produced by the step 5, can be treated by the conventional procedure. If desired, the produced compound is purified by, for example, recrystallization, column chromatography or sublimation.

The production process of the compound of formula (5), used as a starting material in the step 5 in the second production process for producing the 1,3,5-triazine derivative of formula (1) according to the present invention, will now be described.

The compound of formula (5) can be produced, for example, through the reaction scheme illustrated in the following step 6.

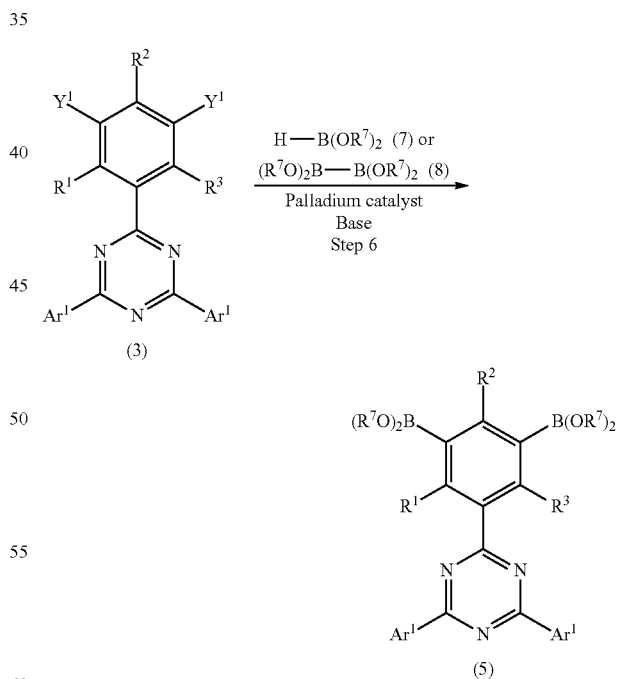

In the general formulae (3), (8) and (5), $R^1$, $R^2$ and $R^3$ each independently represent a hydrogen atom or a methyl group. $Ar^1$ represents a substituted or unsubstituted aromatic hydrocarbon group. $Y^1$ represents a chlorine atom, a bromine atom, an iodine atom or a trifluoromethanesulfoxy group. Fe represents a hydrogen atom, an alkyl group having 1 to 4 carbon atoms or a phenyl group, and the two R⁷s may be the same or different, and the two R⁷s can form a ring together with the boron atom bonded to the two R⁷s via the respective oxygen atoms.

The step 6 is a step of allowing the compound of formula (3) to react with the borane compound of formula (7) or the diboron compound of formula (8) in the presence of a base and a palladium catalyst to give a compound of the general formula (5), used in the step 5. This reaction can be effected with a high reaction yield of the target compound by adopting reaction conditions and catalysts, which are described in The Journal of Organic Chemistry, vol. 60, 7508-7510, 1995, or The Journal of Organic Chemistry, vol. 65, 164-168, 2000.

The molar ratio of the palladium catalyst to the compound of formula (3) is preferably in the range of 1:200 to 1:2, and more preferably 1:100 to 1:10 because of high reaction yield.

The compound of formula (5) produced can be isolated after the reaction, or used directly for the step 5 without isolation.

As examples of the palladium catalyst used in the step 6, those which are recited as examples thereof used in the step 1 are mentioned. In view of the ease in availability and the reaction yield, palladium chloride, palladium acetate, tris(dibenzylideneacetone)dipalladium, dichlorobis(triphenylphosphine)palladium, tetrakis(triphenylphosphine)palladium and dichloro[1,1'-bis(diphenylphosphino)ferrocene]palladium are preferable.

Of these, palladium complex compounds having a tertiary phosphine as a ligand are especially preferable because of high reaction yield. The palladium complex compounds having a tertiary phosphine as a ligand can also be prepared in a reaction system comprising a palladium salt or a palladium complex compound, and a tertiary phosphine added therein.

As specific examples of the tertiary phosphine used, those which are recited as examples thereof used in the step 1 are mentioned. In view of the ease in availability and high reaction yield, triphenylphosphine and 1,1'-bis(diphenylphosphino)-ferrocene are preferable.

The molar ratio of the tertiary phosphine to the palladium salt or the palladium complex compound is preferably in the range of 1:10 to 10:1, and more preferably 1:2 to 5:1 because of high reaction yield.

As examples of the base used in the step 6, those which are recited as examples thereof used in the step 1 are mentioned. In view of high reaction yield, potassium acetate is preferable. The molar ratio of the base to the compound of formula (3) is preferably in the range of 1:2 to 10:1, and more preferably 1:1 to 3:1 because of high reaction yield.

The molar ratio of the borane compound of formula (7) or the diboron compound of formula (8) to the compound of formula (3) is preferably in the range of 1:1 to 5:1, and more preferably 2:1 to 4:1 because of high reaction yield.

The step 6 can be effected in a reaction medium. The reaction medium used includes, for example, dimethylsulfoxide, tetrahydrofuran, toluene, benzene, diethyl ether and xylene. These reaction mediums may be used either alone or in combination. Of these, tetrahydrofuran is preferable because of high reaction yield.

The reaction in the step 6 can be effected at a temperature appropriately chosen in a range of 0° C. to 150° C. A temperature of 50° C. to 120° C. is especially preferable because of high reaction yield.

The compound of formula (5), produced by the step 6, can be treated by the conventional procedure. If desired, the produced compound is purified by, for example, recrystallization, column chromatography or sublimation.

The 1,3,5-triazine derivative of formula (1) according to the present invention is usually used in a thin film form for an organic electroluminescent device. The process for producing a thin film of the 1,3,5-triazine derivative of formula (1) for an organic electroluminescent device is not particularly limited. For example, vacuum deposition can be adopted for the formation of the thin film. The vacuum deposition can be conducted using a conventional vacuum deposition apparatus. However, in consideration of the tact time and cost for the production of the organic electroluminescent device, the degree of vacuum at the vacuum deposition is preferably in the range of approximately $1 \times 10^{-2}$ Pa to $1 \times 10^{-5}$ Pa which can be achieved by the conventionally used diffusion pump, turbo-molecular pump or cryopump. The rate of vacuum deposition varies depending upon the thickness of thin film, but the rate is preferably in the range of 0.005 nm/sec to 1.0 nm/sec.

The solubility of the 1,3,5-triazine derivative of formula (1) in a solvent such as chloroform, dichloromethane, 1,2-dichloroetane, chlorobenzene, toluene, ethyl acetate or tetrahydrofuran is high. Therefore, the thin film can also be formed from a solution thereof by, for example, spin coating, ink jetting, casting or dipping using the conventional apparatus.

EXAMPLES

Example 1

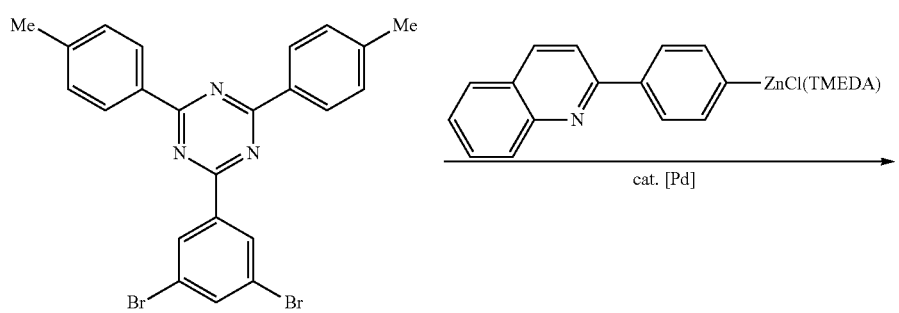

-continued

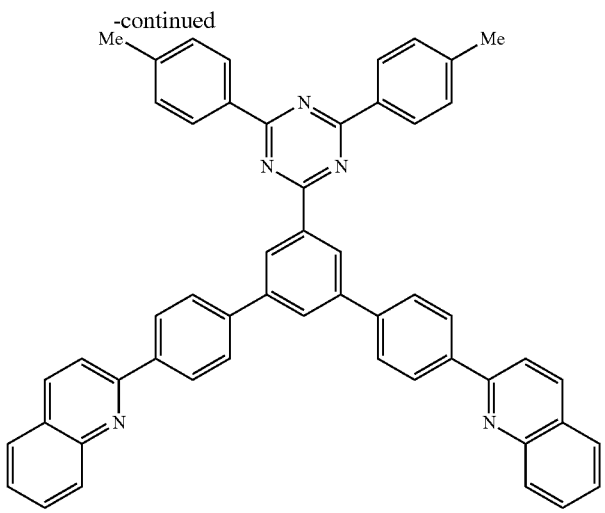

In a stream of argon, 2.58 g (9.09 mmol) of 2-(4-bromophenyl)quinoline was dissolved in 20 mL of tetrahydrofuran. To the thus-obtained solution, 6.01 mL of a solution in hexane of 9.70 mmol of butyllithium was dropwise added at −78° C. The resultant mixture was stirred at −78° C. for 15 minutes, and then 2.45 g (9.70 mmol) of dichloro(tetramethylethylenediamine)zinc(II) was added. Temperature of the resultant mixture was elevated to room temperature, and stirred for 1.5 hours. The resultant mixture, and 1.50 g (3.03 mmol) of 2-(3,5-dibromophenyl)-4,6-di-p-tolyl-1,3,5-triazine, and 420 mg (0.364 mmol) of tetrakis(triphenylphosphine)palladium were suspended in 30 mL of tetrahydrofuran, and the obtained suspension was heated under reflux with stirring for 15 hours. The reaction mixture was cooled to room temperature, and was then distilled under a reduced pressure to remove low boiling ingredients. Methanol was added to the concentrate and the thus-deposited solid was filtered. The thus-obtained crude product was purified by silica gel chromatography using a methanol/chloroform (1:100-2:100) mixed liquid as a developing solvent to give 2.03 g of the target 2-[4,4''-di(2-quinolyl)-1,1':3',1''-terphenyl-5-yl]-4,6-di-p-tolyl-1,3,5-triazine as a white solid (yield: 90%).

$^1$H-NMR (CDCl$_3$): δ2.43 (s, 6H), 7.33 (d, J=8.0 Hz, 4H), 7.49 (t, J=7.1 Hz, 2H), 7.67-7.72 (m, 2H), 7.79 (d, J=7.9 Hz, 2H), 7.93 (d, J=8.1 Hz, 6H), 8.12 (t, J=1.7 Hz, 1H), 8.14 (d, J=5.7 Hz, 2H), 8.21 (d, J=8.5 Hz, 2H), 8.32 (d, J=8.2 Hz, 4H), 8.64 (d, J=8.0 Hz, 4H), 9.01 (d, J=1.6 Hz, 2H).

Example 2

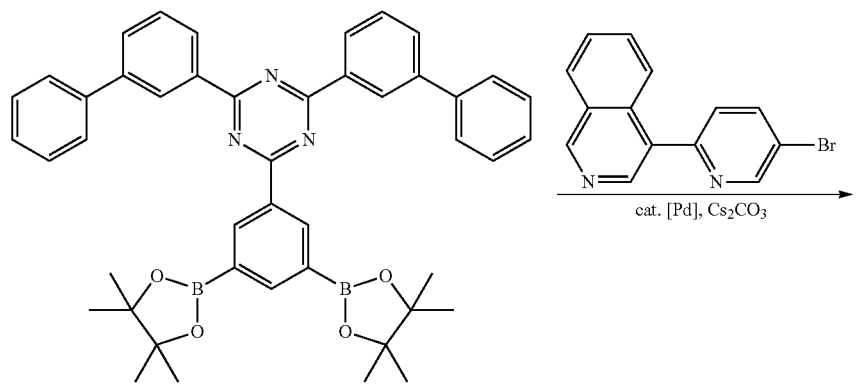

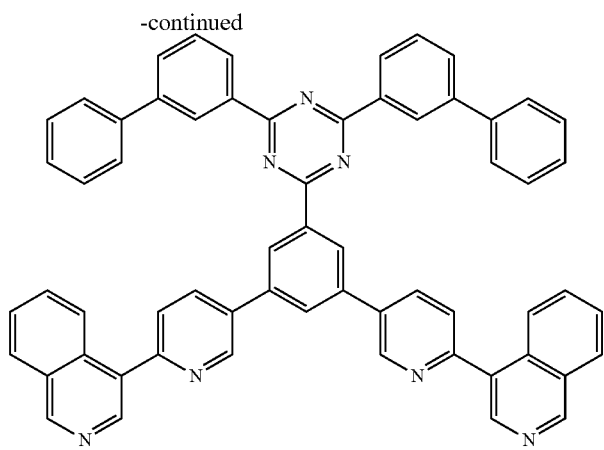

In a stream of argon, 219 mg (0.77 mmol) of 4-(5-bromopyridin-2-yl)isoquinoline, 271 mg (0.38 mmol) of 2-[3,5-bis(4,4,5,5-tetramethyl-1,3,2-dioxabororan-2-yl)phenyl]-4,6-bis(3-biphenylyl)-1,3,5-triazine, 251 mg (0.77 mmol) of cesium carbonate and 5 mg (0.008 mmol) of dichlorobis-triphenylphosphine)palladium were suspended in 20 mL of tetrahydrofuran, and the obtained suspension was heated under reflux for 65 hours. The reaction mixture was cooled to room temperature, and was then distilled under a reduced pressure to remove low boiling ingredients. Methanol was added to the concentrate and the thus-deposited solid was filtered. The thus-obtained crude product was purified by silica gel chromatography using a methanol/chloroform (0:100-2:100) mixed liquid as a developing solvent to give 151 mg of the target 2,4-bis(3-biphenylyl)-6-{3,5-bis[6-(4-isoquinolyl)pyridin-3-yl]phenyl}-1,3,5-triazine as a white solid (yield: 46%).

$^1$H-NMR (CDCl$_3$): δ7.31-7.38 (m, 2H), 7.42-7.49 (m, 4H), 7.59-7.68 (m, 4H), 7.67-7.76 (m, 6H), 7.75-7.84 (m, 4H), 8.04 (d, J=8.1, 2.5 Hz, 2H), 8.17 (brs, 1H), 8.27 (dt, J=8.1, 3.1 Hz, 2H), 8.32 (dd, J=8.4, 3.4 Hz, 2H), 8.71 (d, J=3.9 Hz, 2H), 8.76 (brd, J=7.5 Hz, 2H), 9.00-8.98 (m, 2H), 9.11-9.14 (m, 2H), 9.25 (brs, 2H), 9.29 (d, J=3.4 Hz, 2H).

Example 3

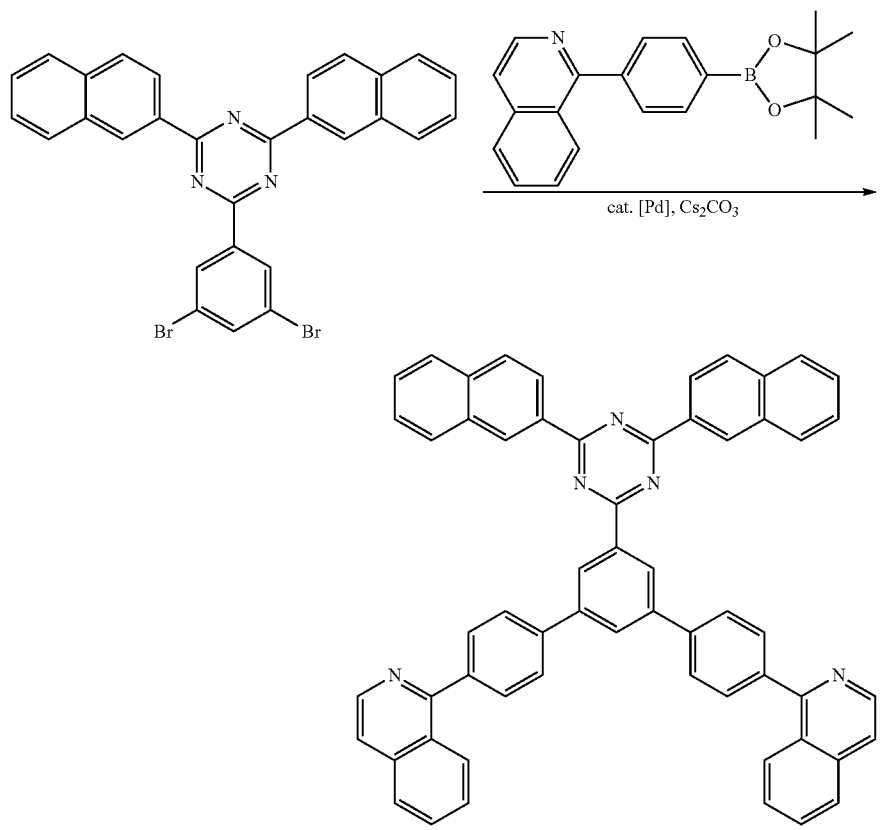

In a stream of argon, 1.00 g (1.76 mmol) of 2-[3,5-dibromophenyl]-4,6-di(2-naphthyl)-1,3,5-triazine, 1.48 g (3.88 mmol) of 1-[4-(4,4,5,5-tetramethyl-1,3,2-dioxabororan-2-yl)phenyl]isoquinoline, 1.26 g (3.87 mmol) of cesium carbonate, 17 mg (0.078 mmol) of palladium acetate and 74 mg (0.16 mmol) of 2-dicyclohexylphosphino-2',4',6'-triisopropylbiphenyl were suspended in 15 mL of tetrahydrofuran, and the obtained suspension was heated under reflux for 12 hours. The reaction mixture was cooled to room temperature, and was then distilled under a reduced pressure to remove low boiling ingredients. Methanol was added to the concentrate and the thus-deposited solid was filtered. The thus-obtained crude product was purified by silica gel chromatography using chloroform as a developing solvent to give 501 mg of the target 2-[4,4''-di(1-isoquinolyl)-1,1':3',1''-terphenyl-5'-yl]-4,6-di(2-naphthyl)-1,3,5-triazine as a yellow solid (yield: 35%).

$^1$H-NMR (CDCl$_3$): δ.7.38-7.51 (m, 4H), 7.46-7.63 (m, 4H), 7.64-7.89 (m, 12H), 7.89 (d, J=7.8 Hz, 4H), 7.99 (s, 1H), 8.13 (d, J=8.3 Hz, 2H), 8.52 (d, J=5.8 Hz, 2H), 8.63 (d, J=8.3 Hz, 2H), 8.91 (brs, 2H), 9.10 (brs, 2H).

$^{13}$C-NMR (CDCl$_3$): δ120.1 (CH×2), 125.3 (CH×2), 126.5 (CH×2), 126.8 (quart.×2), 127.0 (CH×2), 127.1 (CH×2), 127.2 (CH×2), 127.4 (CH×2), 127.5 (CH×4), 127.6 (CH×2), 127.9 (CH×2), 128.4 (CH×2), 129.8 (CH×2), 130.1 (CH×2), 130.2 (CH×2), 130.6 (CH), 130.7 (CH×4), 133.2 (quart.×2), 133.6 (quart.×2), 135.8 (quart.×2), 137.0 (quart.×2), 137.7 (quart.), 139.1 (quart.×2), 141.1 (quart.×2), 141.9 (quart.×2), 142.4 (CH×2), 160.4 (quart.×2), 171.4 (quart.), 171.8 (quart.×2).

Example 4

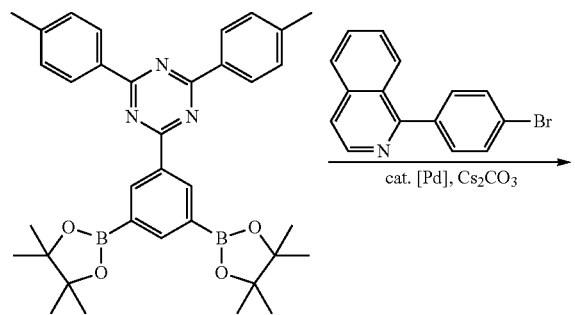
cat. [Pd], Cs$_2$CO$_3$

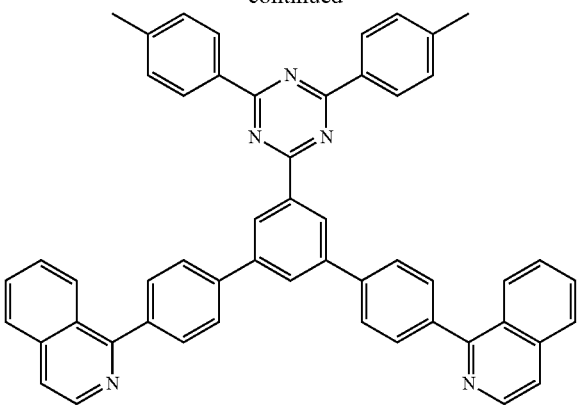

In a stream of argon, 1.13 g (3.56 mmol) of 1-(4-bromophenyl)isoquinoline, 1.00 mg (1.70 mmol) of 2-[3,5-bis(4,4,5,5-tetramethyl-1,3,2-dioxabororan-2-yl)phenyl]-4,6-di-p-tolyl-1,3,5-triazine, 1.11 g (3.40 mmol) of cesium carbonate and 100 mg (0.14 mmol) of dichlorobistriphenylphosphine)palladium were suspended in 40 mL of tetrahydrofuran, and the obtained suspension was heated under reflux for 15 hours. The reaction mixture was cooled to room temperature, and was then distilled under a reduced pressure to remove low boiling ingredients. Methanol was added to the concentrate and the thus-deposited solid was filtered. The thus-obtained crude product was purified by silica gel chromatography using chloroform as a developing solvent to give 263 mg of the target 2-[4,4''-di(1-isoquinolyl)-1,1':3',1''-terphenyl-5'-yl]-4,6-di-p-tolyl-1,3,5-triazine as a white solid (yield: 35%).

$^1$H-NMR (CDCl$_3$): δ2.43 (s, 6H), 7.34 (d, J=8.0 Hz, 4H), 7.55 (ddd, J=8.4, 3.5, 1.4 Hz, 2H), 7.61-7.71 (m, 2), 7.63 (d, J=5.8 Hz, 2H), 7.81-7.90 (m, 2H), 7.85 (d, J=8.3 Hz, 4H), 7.95 (d, J=8.3 Hz, 4H), 8.15 (t, J=1.8 Hz, 1H), 8.21 (d, J=7.8 Hz, 2H), 8.61 (d, J=5.8 Hz, 2H), 8.65 (d, J=8.3 Hz, 4H), 9.03 (d, J=1.8 Hz, 2H).

Example 5

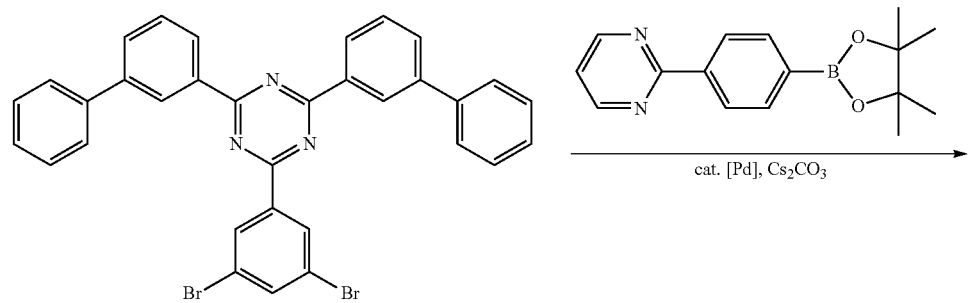
cat. [Pd], Cs$_2$CO$_3$

-continued

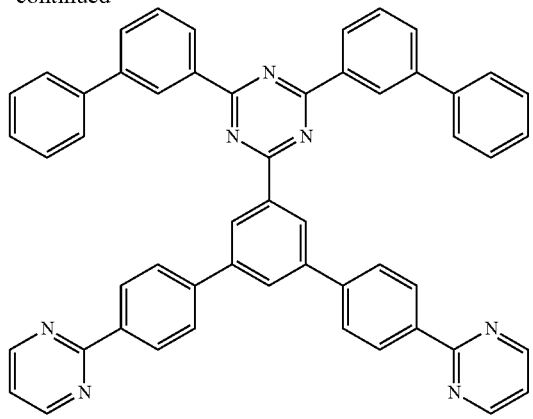

In a stream of argon, 0.98 g (3.48 mmol) of 2-[4-(4,4,5,5-tetramethyl-1,3,2-dioxabororan-2-yl)phenyl]pyrimidine, 0.98 g (1.58 mmol) of 2-(3,5-dibromophenyl)-4,6-bis(3-biphenylyl)-1,3,5-triazine, 1.13 g (3.48 mmol) of cesium carbonate, 7.2 mg (0.032 mmol) of palladium acetate and 30.5 g (0.031 mmol) of 2-dicyclohexylphosphino-2',4',6'-triisopropylbiphenyl were suspended in 95 mL of tetrahydrofuran, and the obtained suspension was heated under reflux for 17 hours. The reaction mixture was cooled to room temperature, and was then distilled under a reduced pressure to remove low boiling ingredients. Methanol was added to the concentrate and the thus-deposited solid was filtered. The thus-obtained crude product was purified by silica gel chromatography using a hexane/chloroform (1:6) mixed liquid as a developing solvent to give 0.85 g of the target 2-[4,4''-di(2-pyrimidyl)-1,1':3',1''-terphenyl-5-yl]-4,6-bis(3-biphenylyl)-1,3,5-triazine as a white solid (yield: 67%).

$^1$H-NMR (CDCl$_3$): δ7.13 (t, J=4.9 Hz, 2H), 7.36 (t, J=7.3 Hz, 2H), 7.46 (t, J=7.1 Hz, 4H), 7.61 (J=7.6 Hz, 2H), 7.65-7.75 (m, 6H), 7.79 (d, J=6.3 Hz, 2H), 8.21 (bs, 1H), 8.37 (d, J=8.3 Hz, 4H), 8.68-8.83 (m, 8H), 8.94 (bs, 2H), 9.02 (bs, 2H).

Example 6

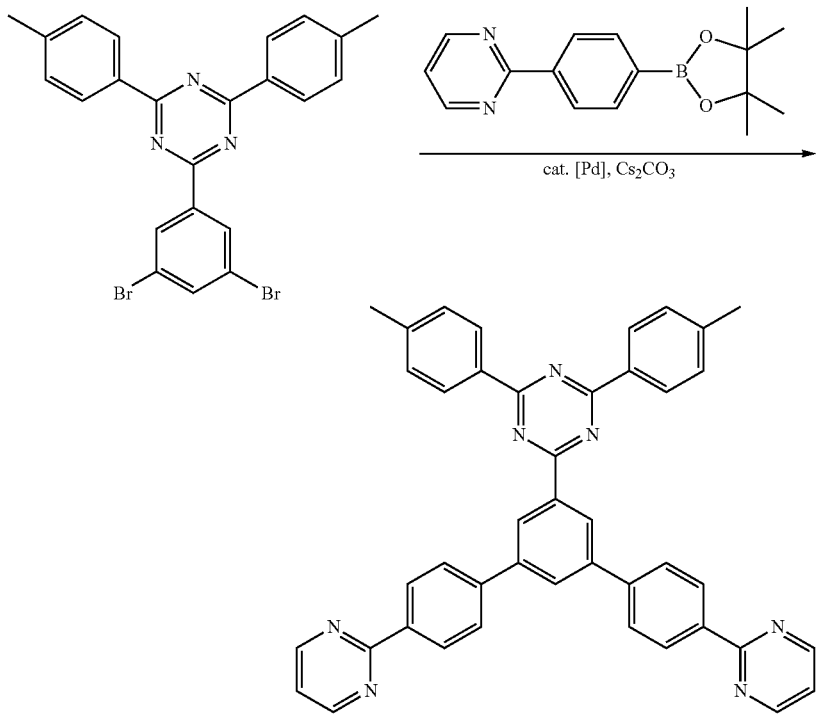

In a stream of argon, 1.95 g (5.54 mmol) of 2-[4-(4,4,5,5-tetramethyl-1,3,2-dioxabororan-2-yl)phenyl]pyrimidine, 1.34 g (2.70 mmol) of 2-(3,5-dibromophenyl)-4,6-di(p-tolyl)-1,3,5-triazine, 1.81 g (5.54 mmol) of cesium carbonate and 38 mg (0.054 mmol) of dichlorobis(triphenylphosphine)palladium(II) were suspended in 100 mL of tetrahydrofuran, and the obtained suspension was heated under reflux for 23 hours. The reaction mixture was cooled to room temperature, and was then distilled under a reduced pressure to remove low boiling ingredients. Methanol was added to the concentrate and the thus-deposited solid was filtered. The thus-obtained crude product was purified by silica gel chromatography using a methanol/chloroform (1:100) mixed liquid as a developing solvent to give 1.59 g of the target 2-[4,4"-di(2-pyrimidyl)-1,1':3',1"-terphenyl-5'-yl]-4,6-di-p-tolyl-1,3,5-triazine as a white solid (yield: 91%).

$^1$H-NMR (CDCl$_3$): δ2.53 (s, 6H), 7.25 (t, J=4.9 Hz, 4H), 7.43 (d, J=8.0 Hz, 4H), 8.00 (d, J=8.3 Hz, 4H), 8.21 (bs, 1H), 8.68 (d, J=7.8 Hz, 4H), 8.73 (d, J=8.0 Hz, 4H), 8.90 (d, J=5.3 Hz, 4H), 9.10 (bs, 2H).

Example 7 bonate and 15 mg (0.021 mmol) of dichlorobis(triphenylphosphine)palladium(II) were suspended in 60 mL of tetrahydrofuran, and the obtained suspension was heated under reflux for 15 hours. The reaction mixture was cooled to room temperature, and was then distilled under a reduced pressure to remove low boiling ingredients. Methanol was added to the concentrate and the thus-deposited solid was filtered. The thus-obtained crude product was purified by silica gel chromatography using chloroform as a developing solvent to give 539 mg of the target 2-[4,4"-di(2-pyrimidyl)-1,1':3',1"-terphenyl-5'-yl]-4,6-di(2-naphthyl)-1,3,5-triazine as a yellow solid (yield: 72%).

$^1$H-NMR (CDCl$_3$): δ7.17 (t, J=4.8 Hz, 2H), 7.50-7.57 (m, 4H), 7.89 (d, J=7.5 Hz, 2H), 7.93 (d, J=8.3 Hz, 4H), 7.99 (d, J=8.6 Hz, 2H), 8.08 (d, J=7.4 Hz, 2H), 8.14 (t, J=1.7 Hz, 1H),

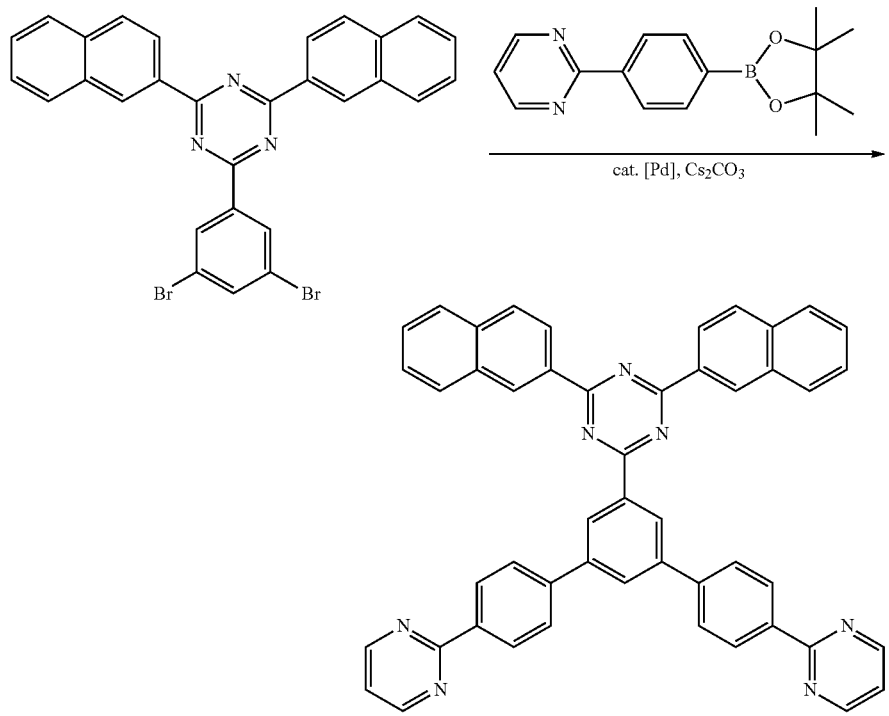

In a stream of argon, 659 mg (2.16 mmol) of 2-[4-(4,4,5,5-tetramethyl-1,3,2-dioxaboroan-2-yl)phenyl]pyrimidine, 596 mg (1.05 mmol) of 2-(3,5-dibromophenyl)-4,6-di(2-naphthyl)-1,3,5-triazine, 704 mg (2.16 mmol) of cesium carbonate 8.59 (d, J=8.3 Hz, 4H), 8.81 (d, J=4.8 Hz, 2H), 8.83 (dd, J=8.5, 1.5 Hz, 2H), 9.09 (d, J=1.7 Hz, 2H), 9.34 (s, 2H).

Example 8

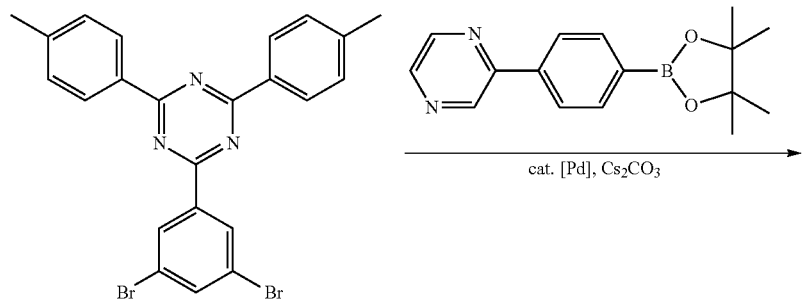

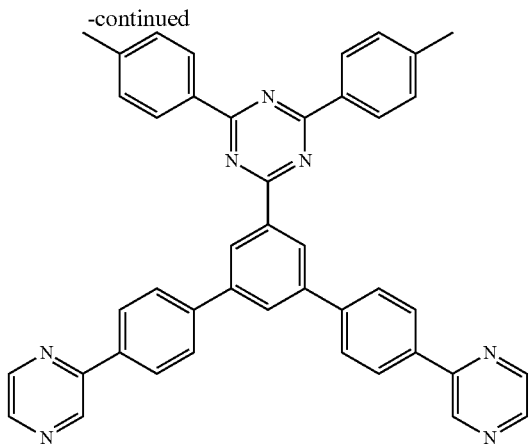

In a stream of argon, 289 mg (1.03 mmol) of 2-[4-(4,4,5,5-tetramethyl-1,3,2-dioxabororan-2-yl)phenyl]pyrazine, 248 mg (0.50 mmol) of 2-(3,5-dibromophenyl)-4,6-di-p-tolyl-1,3,5-triazine, 334 mg (1.03 mmol) of cesium carbonate and 7 mg (0.010 mmol) of dichlorobis(triphenylphosphine)palladium(II) were suspended in 30 mL of tetrahydrofuran, and the obtained suspension was heated under reflux for 17 hours. The reaction mixture was cooled to room temperature, and was then distilled under a reduced pressure to remove low boiling ingredients. Methanol was added to the concentrate and the thus-deposited solid was filtered. The thus-obtained crude product was purified by silica gel chromatography using a hexane/chloroform (10:80) mixed liquid as a developing solvent to give 250 mg of the target 2-[4,4''-di(2-pyrazyl)-1,1':3',1''-terphenyl-5'-yl]-4,6-di-p-tolyl-1,3,5-triazine as a white solid (yield: 77%).

$^1$H-NMR (CDCl$_3$): δ2.43 (s, 6H), 7.33 (d, J=8.0 Hz, 4H), 7.91 (d, J=8.3 Hz, 4H), 8.08 (t, J=1.8 Hz, 1H), 8.17 (d, J=8.3 Hz, 4H), 8.49 (d, J=2.5 Hz, 2H), 8.58-8.67 (m, 6H), 8.99 (d, J=1.8 Hz, 2H), 9.08 (d, J=1.5 Hz, 2H).

Example 9

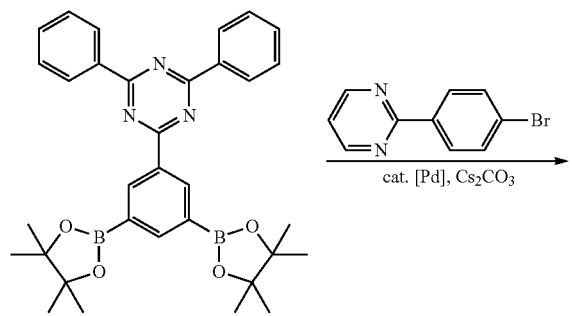

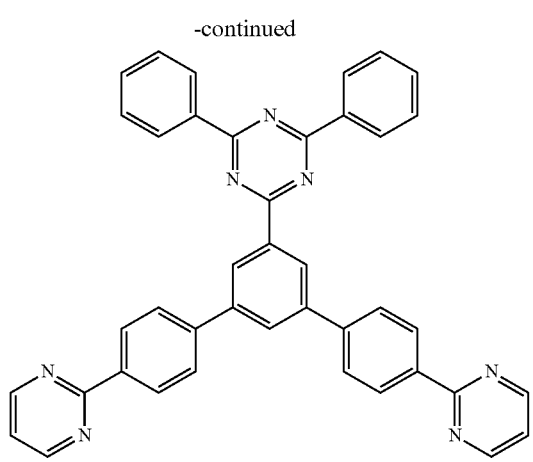

In a stream of argon, 1.00 g (1.78 mmol) of 2-[3,5-bis(4,4,5,5-tetramethyl-1,3,2-dioxabororan-2-yl)phenyl]-4,6-diphenyl-1,3,5-triazine, 0.88 g (3.74 mmol) of 2-(4-bromophenyl)pyrimidine, 1.16 g (3.56 mmol) of cesium carbonate and 105 mg (0.150 mmol) of dichlorobis-(triphenylphosphine)palladium were suspended in 35 mL of tetrahydrofuran, and the obtained suspension was heated under reflux for 17 hours. The reaction mixture was cooled to room temperature, and was then distilled under a reduced pressure to remove low boiling ingredients. Methanol was added to the concentrate and the thus-deposited solid was filtered. The thus-obtained crude product was purified by silica gel chromatography using a hexane/chloroform (50:50) mixed liquid as a developing solvent to give 0.38 g of the target 2,4-diphenyl-6-[4,4''-di(2-pyrimidyl)-1,1':3',1''-terphenyl-5'-yl]-1,3,5-triazine as a white solid (yield: 29%).

$^1$H-NMR (CDCl$_3$): δ7.16 (t, J=4.8 Hz, 2H), 7.50-7.60 (m, 6H), 7.89 (d, J=8.3 Hz, 4H), 8.12 (t, J=1.6 Hz, 1H), 8.57 (d, J=8.3 Hz, 4H), 8.75 (dd, J=8.2, 1.6 Hz, 4H), 8.79 (d, J=4.8 Hz, 4H), 9.01 (d, J=1.7 Hz, 2H).

$^{13}$C-NMR (CDCl$_3$): δ119.2 (CH×2), 127.1 (CH×2), 127.8 (CH×4), 128.8 (CH×4), 128.9 (CH×4), 129.1 (CH×4), 130.1 (CH), 132.7 (CH×2), 136.2 (quart.×2), 137.2 (quart.×2), 137.6 (quart.), 141.8 (quart.×2), 143.0 (quart.×2), 157.4 (CH×4), 164.6 (quart.×2), 171.5 (quart.), 171.8 (quart.×2).

¹H-NMR (CDCl₃): δ7.50-7.59 (m, 6H), 7.63-7.78 (m, 4H), 7.99 (d, J=7.7 Hz, 4H), 8.10 (d, J=8.2 Hz, 2H), 8.15-8.16 (m, 3H), 8.37 (d, J=7.8 Hz, 4H), 8.77 (d, J=7.4 Hz, 4H), 9.06 (s, 2H), 9.39 (s, 2H).

Example 10

Example 11

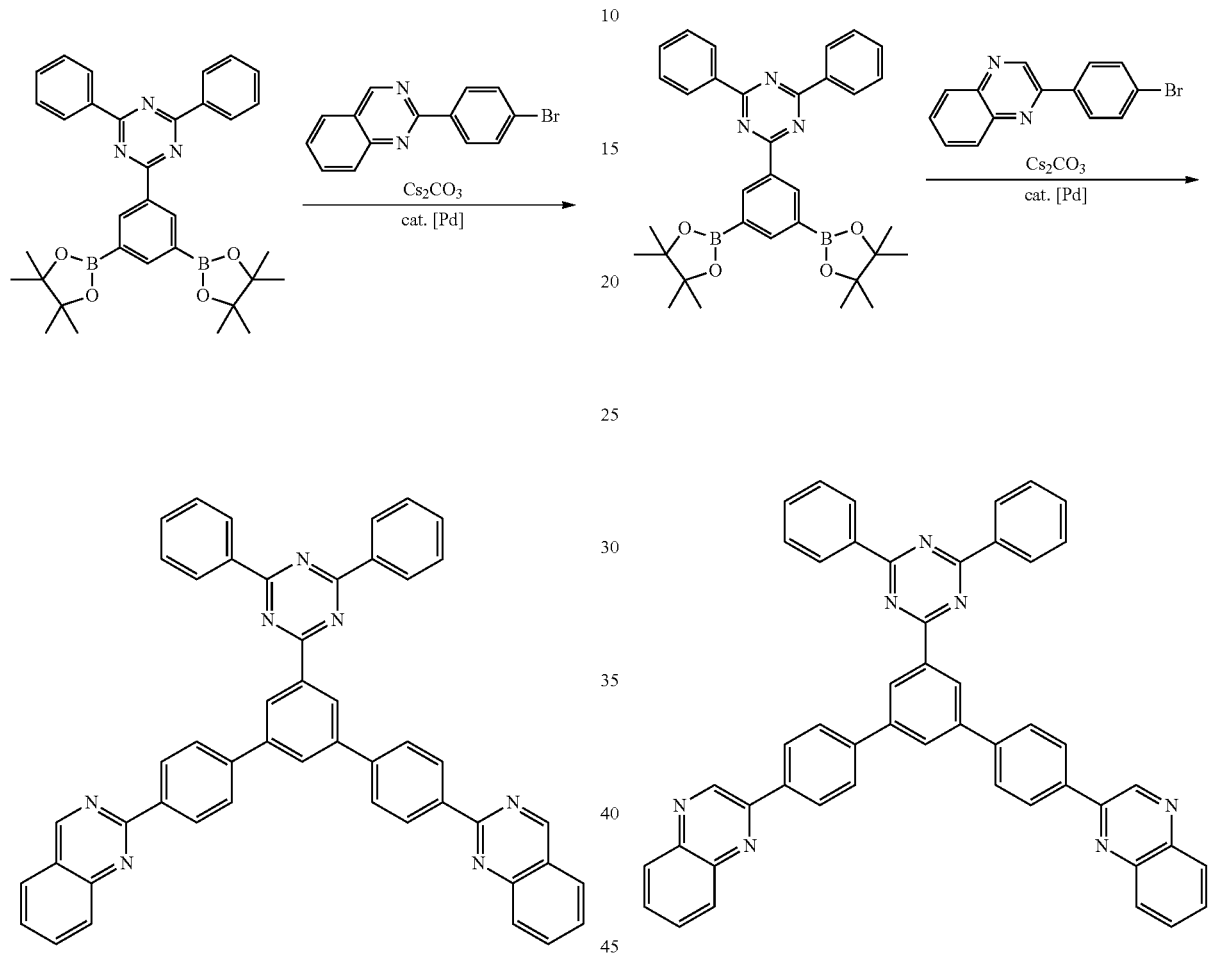

In a stream of argon, 1.00 g (1.78 mmol) of 2-[3,5-bis(4,4,5,5-tetramethyl-1,3,2-dioxabororan-2-yl)phenyl]-4,6-diphenyl-1,3,5-triazine, 1.27 g (4.45 mmol) of 2-(4-bromophenyl)quinazoline, 1.16 g (3.56 mmol) of cesium carbonate and 250 mg (0.356 mmol) of dichlorobis-(triphenylphosphine)palladium were suspended in 30 mL of tetrahydrofuran, and the obtained suspension was heated under reflux for 65 hours. The reaction mixture was cooled to room temperature, and was then distilled under a reduced pressure to remove low boiling ingredients. Methanol was added to the concentrate and the thus-deposited solid was filtered. The thus-obtained crude product was purified by silica gel chromatography using a hexane/chloroform (1:4) mixed liquid as a developing solvent to give 0.78 g of the target 2,4-diphenyl-6-[4,4"-di(2-quinazolyl)-1,1':3',1"-terphenyl-5'-yl]-1,3,5-triazine as a white solid (yield: 63%).

In a stream of argon, 1.00 g (1.78 mmol) of 2-[3,5-bis(4,4,5,5-tetramethyl-1,3,2-dioxabororan-2-yl)phenyl]-4,6-dihenyl-1,3,5-triazine, 1.27 g (4.45 mmol) of 2-(4-bromophenyl)quinoquixaline, 1.16 g (3.56 mmol) of cesium carbonate and 250 mg (0.356 mmol) of dichlorobis-(triphenylphosphine) palladium were suspended in 30 mL of tetrahydrofuran, and the obtained suspension was heated under reflux for 64 hours. The reaction mixture was cooled to room temperature, and was then distilled under a reduced pressure to remove low boiling ingredients. Methanol was added to the concentrate and the thus-deposited solid was filtered. The thus-obtained crude product was purified by silica gel chromatography using a hexane/chloroform (1:4) mixed liquid as a developing solvent to give 0.70 g of the target 2,4-diphenyl-6-[4,4"-di(2-quinoxalyl)-1,1':3',1"-terphenyl-5'-yl]-1,3,5-triazine as a white solid (yield: 55%).

¹H-NMR (CDCl₃): δ7.50-7.59 (m, 6H), 7.63-7.78 (m, 6H), 7.99 (d, J=7.7 Hz, 4H), 8.10 (d, J=8.2 Hz, 2H), 8.15 (t, J=1.8 Hz, 1H), 8.46 (d, J=7.7 Hz, 4H), 8.77 (d, J=7.6 Hz, 4H), 9.04 (s, 2H), 9.38 (s, 2H).

Reference Example 1

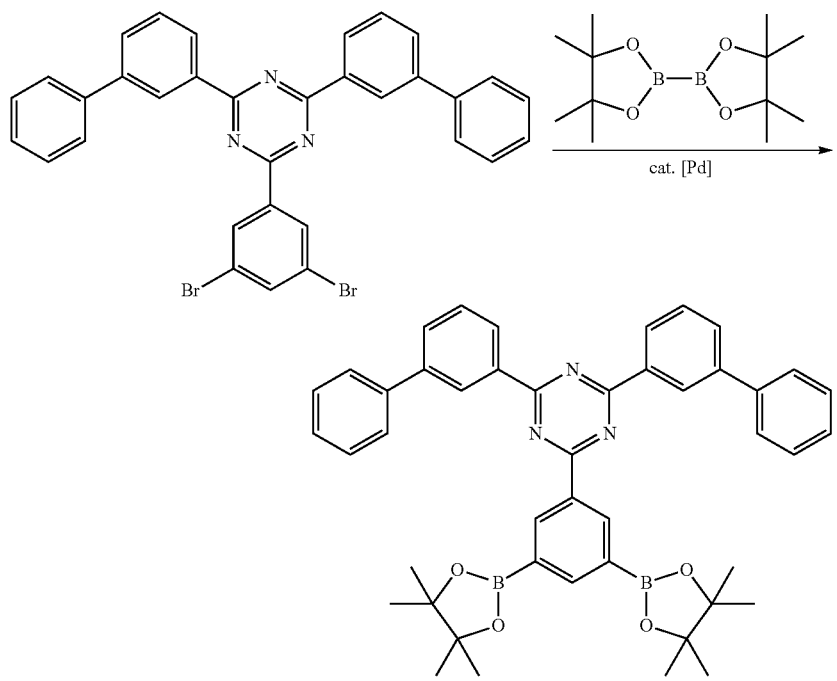

In a stream of argon, 310 mg (0.50 mmol) of 2,4-bis(3-biphenylyl)-6-(3,5-dibromophenyl)-1,3,5-triazine, 305 mg (1.20 mmol) of bis(pinacolato)diboron, 236 mg (2.40 mmol) of potassium acetate and 18 mg (0.025 mmol) of dichlorobis-(triphenylphosphine)palladium were suspended in 20 mL of tetrahydrofuran, and the obtained suspension was heated under reflux for 18 hours. The reaction mixture was cooled to room temperature, and was then distilled under a reduced pressure to remove low boiling ingredients. Methanol was added to the concentrate and the thus-deposited solid was filtered. The thus-obtained crude product was purified by silica gel chromatography using chloroform as a developing solvent to give 305 mg of the target 2,4-bis(3-biphenylyl)-6-[3,5-bis(4,4,5,5-tetramethyl-1,3,2-dioxabororan-2-yl)phenyl]-1,3,5-triazine as a white solid (yield: 85%).

$^1$H-NMR (CDCl$_3$): δ1.34 (s, 24H), 7.35 (brt, J=7.3 Hz, 2H), 7.45 (brt, J=7.3 Hz, 4H), 7.61 (t, J=7.7 Hz, 2H), 7.73 (brd, J=7.3 Hz, 4H), 7.80 (brddd, J=7.7, 1.6, 1.6 Hz, 2H), 8.45 (brs, 1H), 8.73 (brddd, J=7.7, 1.6, 1.6 Hz, 2H), 9.02 (brt, J=1.6 Hz, 2H), 9.22 (d, J=1.2 Hz, 2H).

Reference Example 2

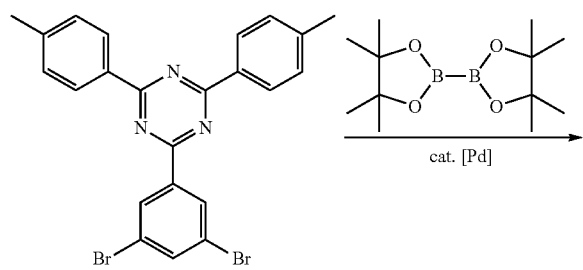

-continued

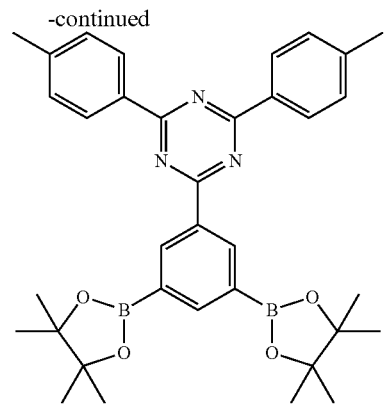

In a stream of argon, 1.43 g (2.88 mmol) of 2,4-di-p-tolyl-6-(3,5-dibromophenyl)-1,3,5-triazine, 3.00 g (11.8 mmol) of bis(pinacolato)diboron, 1.70 g (17.3 mmol) of potassium acetate and 81 mg (0.12 mmol) of dichlorobis-(triphenylphosphine)palladium were suspended in 30 mL of tetrahydrofuran, and the obtained suspension was heated under reflux for 15 hours. The reaction mixture was cooled to room temperature, and was then distilled under a reduced pressure to remove low boiling ingredients. Methanol was added to the concentrate and the thus-deposited solid was filtered. The thus-obtained crude product was purified by silica gel chromatography using a hexane/chloroform (1:1) mixed liquid as a developing solvent to give 1.68 g of the target 2,4-di-p-tolyl-6-[3,5-bis(4,4,5,5-tetramethyl-1,3,2-dioxabororan-2-yl)-phenyl]-1,3,5-triazine as a white solid (yield: 99%).

$^1$H-NMR (CDCl$_3$): δ1.34 (s, 24H), 2.41 (s, 6H), 7.32 (d, J=8.0 Hz, 4H), 8.43 (t, J=1.3 Hz, 1H), 8.63 (d, J=8.3 Hz, 4H), 9.13 (d, J=1.3 Hz, 2H).

Reference Example 3

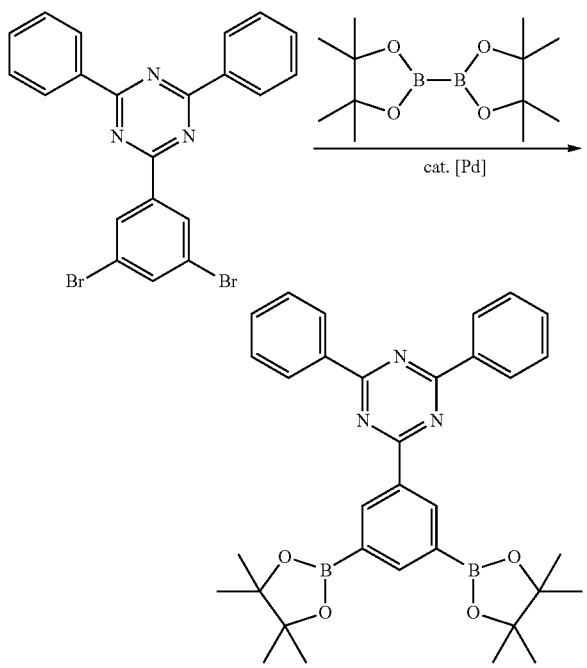

In a stream of argon, 5.00 g (10.7 mmol) of 2-(3,5-dibromophenyl)-4,6-diphenyl-1,3,5-triazine, 5.98 g (23.5 mmol) of bis(pinacolato)diboron, 4.62 g (47.1 mmol) of potassium acetate and 300 mg (0.428 mmol) of dichlorobis-(triphenylphosphine)palladium were suspended in 30 mL of tetrahydrofuran, and the obtained suspension was heated under reflux for 22 hours. The reaction mixture was cooled to room temperature, and was then distilled under a reduced pressure to remove low boiling ingredients. Methanol was added to the concentrate and the thus-deposited solid was filtered. The thus-obtained crude product was purified by silica gel chromatography using a hexane/chloroform (1:1) mixed liquid as a developing solvent to give 4.18 g of the target 2-[3,5-bis(4,4,5,5-tetramethyl-1,3,2-dioxabororan-2-yl)phenyl]-1,3,5-triazine as a white solid (yield: 70%).

$^1$H-NMR (CDCl$_3$): δ1.34 (s, 24H), 7.47-7.57 (m, 6H), 8.45 (t, J=1.3 Hz, 1H), 8.70-8.78 (m, 4H), 9.15 (d, J=1.3 Hz, 2H).

Device Example 1

Manufacture of an organic electroluminescent device comprising 1,3,5-triazine derivative, and evaluation thereof.

A glass substrate with an indium-tin oxide (ITO) transparent electrode was prepared, which had a stripe pattern comprised of ITO film with a 2 mm width. The substrate was washed with isopropyl alcohol and then surface-treated by irradiation of ultraviolet rays and generation of ozone. Using the surface-treated substrate, an organic electroluminescent device with an emitting area of 4 mm$^2$ having a multilayer structure as illustrated in FIG. 1 was manufactured as follows.

Each layer was formed by vacuum deposition. The glass substrate was placed in a vacuum deposition chamber, and the inner pressure was reduced to 1.0×10$^{-4}$ Pa.

As illustrated in FIG. 1, on the above-mentioned glass substrate 1, organic compound layers, i.e., a hole injection layer 2, a hole transport layer 3, an emitting layer 4 and an electron transport layer 5 were formed in this order. Further a cathode layer 6 was formed. The hole injection layer 2 was formed by vacuum-depositing phtalocyanine copper(II), previously purified by sublimation, into a thickness of 25 nm. The hole transport layer 3 was formed by vacuum-depositing N,N'-di(naphthylen-1-yl)-N,N'-diphenylbenzidine (NPD) into a thickness of 45 nm.

The emitting layer 4 was formed by vacuum-depositing a mixture of 99 mass % of 4,4'-bis(2,2-diphenylethen-1-yl) diphenyl (DPVBi) and 1 mass % of 4,4'-bis[4-(di-p-tolylamino) phenylethen-1-yl]biphenyl (DPAVBi) into a thickness of 40 nm. The electron transport layer 5 was formed by vacuum-depositing 2-[4,4''-di(2-quinolyl)-1,1':3',1''-terphenyl-5'-yl]-4,6-di-p-tolyl-1,3,5-triazine according to the present invention into a thickness of 20 nm.

The vacuum deposition of each organic material was conducted by subjecting each organic material to electric resistance heating to form a thin film at a deposition rate of 0.3 to 0.5 nm/sec.

Then, a metal mask was arranged so as to be orthogonal to the ITO stripe, and a cathode layer 6 was vacuum-deposited. The vacuum deposition of the cathode layer 6 was conducted so as to have a double layer structure comprising a lithium fluoride layer with a thickness of 0.5 nm and an aluminum layer with a thickness of 100 nm. The measurement of thickness of each organic material thin film layer was conducted by stylus profilometer ("DEKTAK").

Finally the thus-obtained assembly of multi-layers was encapsulated with a glass cap and ultraviolet ray-curable epoxy resin (available from Nagase Chemtex Corporaton). The encapsulation was conducted in a nitrogen atmosphere having an oxygen-and-moisture content of below 1 ppm within a glove box.

Luminous properties of the thus-manufactured blue electroluminescent device were evaluated by applying a direct current using a luminance meter BM-9 available from Topcon Corporation. The luminous properties as measured at a current density of 20 mA/cm$^2$ were as follows. Voltage 5.8 V, luminance 2,480 cd/m$^2$, current efficiency 12.4 cd/A, power efficiency 6.7 lm/W. Luminance half-life of the device was 182 hours.

Device Example 2

By the same procedures as described in Device Example 1, an organic electroluminescent device was manufactured except that an emitting layer 4 was formed by vacuum-depositing tris(8-quinolinolato) aluminum (III) (Alq) into a thickness of 40 nm instead of the emitting layer formed from DPVBi/DPAVBi mixture in Device Example 1.

The thus-manufactured green electroluminescent device exhibited a voltage of 5.6 V, a luminance of 941 cd/m$^2$, a current efficiency of 4.7 cd/A, and a power efficiency of 2.6 lm/W. Luminance half-life of the device was 1,775 hours.

Device Example 3

By the same procedures as described in Device Example 1, an organic electroluminescent device was manufactured except that an electron transport layer 5 was formed by vacuum-depositing 2-[4,4''-di(2-pyrimidyl)-1,1':3',1''-terphenyl-5'-yl]-4,6-di-p-tolyl-1,3,5-triazine into a thickness of 20 nm instead of the electron transport layer formed in Device Example 1.

The thus-manufactured blue electroluminescent device exhibited a voltage of 5.2 V, a luminance of 2,350 cd/m², a current efficiency of 11.8 cd/A, and a power efficiency of 7.0 lm/W. Luminance half-life of the device was 165 hours.

Device Example 4

By the same procedures as described in Device Example 3, an organic electroluminescent device was manufactured except that an emitting layer 4 was formed by vacuum-depositing Alq into a thickness of 40 nm instead of the emitting layer formed from the DPVBi/DPAVBi mixture used in Device Example 3.

The thus-manufactured green electroluminescent device exhibited a voltage of 5.0 V, a luminance of 941 cd/m², a current efficiency of 4.7 cd/A, and a power efficiency of 2.9 lm/W. Luminance half-life of the device was 2,662 hours.

Device Comparative Example 1

By the same procedures as described in Device Example 1, an organic electroluminescent device was manufactured except that an electron transport layer 5 was formed by vacuum-depositing Alq into a thickness of 20 nm instead of the electron transport layer 5 formed from the 1,3,5-triazine derivative in Device Example 1.

The thus-manufactured blue electroluminescent device exhibited a voltage of 7.1V, a luminance of 1,883 cd/m², a current efficiency of 9.4 cd/A, and a power efficiency of 4.2 lm/W. Luminance half-life of the device was 163 hours.

Device Comparative Example 2

By the same procedures as described in Device Example 2, an organic electroluminescent device was manufactured except that an electron transport layer 5 was formed by vacuum-depositing Alq into a thickness of 20 nm instead of the electron transport layer 5 formed from the 1,3,5-triazine derivative in Device Example 2.

The thus-manufactured green electroluminescent device exhibited a voltage of 5.8 V, a luminance of 882 cd/m², a current efficiency of 4.4 cd/A, and a power efficiency of 2.4 lm/W. Luminance half-life of the device was 1,462 hours.

Thus, it was confirmed that the compound of the present invention gives organic electroluminescent devices including a fluorescent device and a phosphorescent device, which exhibit a low power consumption and a long lifetime as compared with the organic electroluminescent devices made of known materials. The compound of the present invention can be applied broadly to organic electroluminescent devices using luminescent materials other than those disclosed in the above examples, which include fluorescent materials and phosphorescent materials. The compound of the present invention may also be applied to coated electroluminescent devices. The organic electroluminescent device of the present invention can be applied broadly to fields including flat panel displays, and lighting equipments to which low power consumption and long lifetime are required.

INDUSTRIAL APPLICABILITY

A film comprising the 1,3,5-triazine derivative of formula (1) according to the present invention has outstanding properties in surface smoothness, amorphousness, heat resistance, electron transportability, hole blocking capability, resistance to oxidation and reduction, moisture resistance, oxygen resistance and electron injection property. Therefore, said film is useful as a material for an organic electroluminescent device, especially as a material for an electron transport layer, a hole blocking layer and a light emitting host layer of an organic electroluminescent device.

Thus, the film comprising the 1,3,5-triazine derivative of formula (1) according to the present invention is highly expected to be utilized as a constituent of an organic electroluminescent device.

The invention claimed is:
1. A 1,3,5-triazine compound represented by the following formula (1):

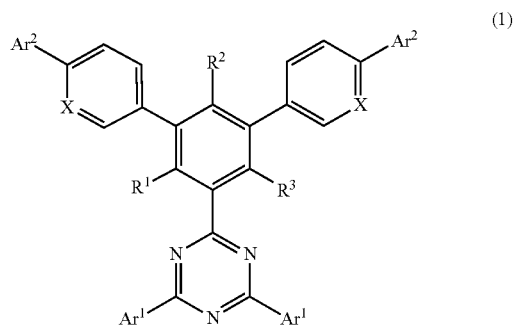

wherein:
$R^1$, $R^2$, and $R^3$ each independently represents a hydrogen atom or a methyl group;
X represents a carbon atom or a nitrogen atom;
$Ar^1$ represents a group selected from a phenyl group, a p-tolyl group, a m-tolyl group, a 4-butylphenyl group, a 4-tert-butylphenyl group, a 4-biphenylyl group, a 3-biphenylyl group, a 1-naphthyl group, a 4-methylnaphthalen-1-yl group, a 4-tert-butylnaphthalen-1-yl group, a 5-methylnaphthalen-1-yl group, a 5-tert-butylnaphthalen-1-yl group, a 2-naphthyl group, a 6-methylnaphthalen-2-yl group, a 6-tert-butylnaphthalen-2-yl group, a 7-methylaphthalene-2-yl group, and a 7-tert-butylnaphthalen-2-yl group; and
$Ar^2$ represents a group selected from a pyrazyl group, which may have an alkyl substituent or substituents, each having 1 to 4 carbon atoms; a 2-pyrimidyl group, which may have an alkyl substituent or substituents, each having 1 to 4 carbon atoms; a 2-quinoxalyl group, which may have an alkyl substituent or substituents, each having 1 to 4 carbon atoms; a quinazolyl group, which may have an alkyl substituent or substituents, each having 1 to 4 carbon atoms; a quinolyl group, which may have an alkyl substituent or substituents, each having 1 to 4 carbon atoms; and an isoquinolyl group, which may have an alkyl substituent or substituents, each having 1 to 4 carbon atoms.

2. The 1,3,5-triazine compound according to claim 1, wherein $R^1$, $R^2$, and $R^3$ represent a hydrogen atom.

3. The 1,3,5-triazine compound according to claim 1, wherein $Ar^1$ represents a substituted or unsubstituted phenyl group, or a substituted or unsubstituted naphthyl group.

4. The 1,3,5-triazine compound according to claim 1, wherein X represents a carbon atom.

5. An organic electroluminescent device comprising as a constituent a 1,3,5-triazine compound represented by the following formula (1):

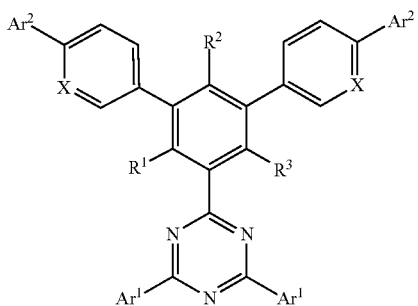

(1)

wherein:

$R^1$, $R^2$, and $R^3$ each independently represents a hydrogen atom or a methyl group;

X represents a carbon atom or a nitrogen atom;

$Ar^1$ represents a group selected from a phenyl group, a p-tolyl group, a m-tolyl group, a 4-butylphenyl group, a 4-tert-butylphenyl group, a 4-biphenylyl group, a 3-biphenylyl group, a 1-naphthyl group, a 4-methylnaphthalen-1-yl group, a 4-tert-butylnaphthalen-1-yl group, a 5-methylnaphthalen-1-yl group, a 5-tert-butylnaphthalen-1-yl group, a 2-naphthyl group, a 6-methylnaphthalen-2-yl group, a 6-tert-butylnaphthalen-2-yl group, a 7-methylaphthalene-2-yl group, and a 7-tert-butylnaphthalen-2-yl group; and $Ar^2$ represents a group selected from a pyrazyl group, which may have an alkyl substituent or substituents, each having 1 to 4 carbon atoms; a 2-pyrimidyl group, which may have an alkyl substituent or substituents, each having 1 to 4 carbon atoms; a 2-quinoxalyl group, which may have an alkyl substituent or substituents, each having 1 to 4 carbon atoms; a quinazolyl group, which may have an alkyl substituent or substituents, each having 1 to 4 carbon atoms; a quinolyl group, which may have an alkyl substituent or substituents, each having 1 to 4 carbon atoms; and an isoquinolyl group, which may have an alkyl substituent or substituents, each having 1 to 4 carbon atoms.

\* \* \* \* \*